US010449152B2

(12) United States Patent
Ohri et al.

(10) Patent No.: US 10,449,152 B2
(45) Date of Patent: Oct. 22, 2019

(54) DRUG LOADED MICROSPHERES FOR POST-OPERATIVE CHRONIC PAIN

(71) Applicant: Covidien LP, Mansfield, MA (US)

(72) Inventors: Rachit Ohri, Framingham, MA (US);
Gary R. Strichartz, Natick, MA (US);
Phillip Blaskovich, Salem, MA (US)

(73) Assignee: Covidien LP, Mansfield, MA (US)

( * ) Notice: Subject to any disclaimer, the term of this patent is extended or adjusted under 35 U.S.C. 154(b) by 163 days.

(21) Appl. No.: 14/848,385

(22) Filed: Sep. 9, 2015

(65) Prior Publication Data
US 2016/0089335 A1 Mar. 31, 2016

Related U.S. Application Data

(60) Provisional application No. 62/056,129, filed on Sep. 26, 2014.

(51) Int. Cl.
A61K 9/16 (2006.01)
A61K 31/445 (2006.01)
A61K 9/00 (2006.01)

(52) U.S. Cl.
CPC .......... A61K 9/1647 (2013.01); A61K 9/0024 (2013.01); A61K 31/445 (2013.01)

(58) Field of Classification Search
None
See application file for complete search history.

(56) References Cited

U.S. PATENT DOCUMENTS

| | | |
|---|---|---|
| 3,364,200 A | 1/1968 | Ashton et al. |
| 3,939,068 A | 2/1976 | Wendt et al. |
| 3,948,666 A | 4/1976 | Kitanishi et al. |
| 4,064,062 A | 12/1977 | Yurko |
| 4,166,800 A | 9/1979 | Fong |
| 4,278,790 A | 7/1981 | McCormick |
| 4,282,236 A | 8/1981 | Broom |
| 4,416,698 A | 11/1983 | McCorsley, III |
| 4,626,253 A | 12/1986 | Broadnax, Jr. |
| 5,057,334 A | 10/1991 | Vail |
| 5,162,430 A | 11/1992 | Rhee et al. |
| 5,324,775 A | 6/1994 | Rhee et al. |
| 5,410,016 A | 4/1995 | Hubbell et al. |
| 5,484,913 A | 1/1996 | Stilwell et al. |
| 5,514,379 A | 5/1996 | Weissleder et al. |
| 5,543,441 A | 8/1996 | Rhee et al. |
| 5,550,187 A | 8/1996 | Rhee et al. |
| 5,747,060 A * | 5/1998 | Sackler ............. A61K 31/165 424/426 |
| 5,752,974 A | 5/1998 | Rhee et al. |
| 5,819,350 A | 10/1998 | Wang |
| 5,874,500 A | 2/1999 | Rhee et al. |
| 5,922,340 A * | 7/1999 | Berde ............. A61K 9/1641 424/426 |
| 6,093,557 A | 7/2000 | Pui et al. |
| 6,152,943 A | 11/2000 | Sawhney |
| 6,156,677 A | 12/2000 | Brown Reed et al. |
| 6,165,201 A | 12/2000 | Sawhney et al. |
| 6,179,862 B1 | 1/2001 | Sawhney |
| 6,217,911 B1 | 4/2001 | Vaugn et al. |
| 6,309,569 B1 | 10/2001 | Farrar et al. |
| 6,399,362 B1 | 6/2002 | Pui et al. |
| 6,500,777 B1 | 12/2002 | Wiseman et al. |
| 6,514,534 B1 | 2/2003 | Sawhney |
| 6,566,406 B1 | 5/2003 | Pathak et al. |
| 6,590,095 B1 | 7/2003 | Schleicher et al. |
| 6,605,294 B2 | 8/2003 | Sawhney |
| 6,627,749 B1 | 9/2003 | Kumar |
| 6,656,200 B2 | 12/2003 | Li et al. |
| 6,673,093 B1 | 1/2004 | Sawhney |
| 6,703,047 B2 | 3/2004 | Sawhney et al. |
| 6,746,869 B2 | 6/2004 | Pui et al. |
| 6,764,720 B2 | 7/2004 | Pui et al. |
| 6,818,018 B1 | 11/2004 | Sawhney |
| 7,009,034 B2 | 3/2006 | Pathak et al. |
| 7,247,338 B2 | 7/2007 | Pui et al. |
| 7,279,322 B2 | 10/2007 | Pui et al. |
| 7,347,850 B2 | 3/2008 | Sawhney |
| 7,498,063 B2 | 3/2009 | Pui et al. |
| 7,595,392 B2 | 9/2009 | Kumar et al. |
| 7,611,494 B2 | 11/2009 | Campbell et al. |
| 7,649,089 B2 | 1/2010 | Kumar et al. |
| 7,662,801 B2 | 2/2010 | Kumar et al. |
| 7,951,248 B1 | 5/2011 | Fallis et al. |
| 8,033,483 B2 | 10/2011 | Fortier et al. |

(Continued)

FOREIGN PATENT DOCUMENTS

| | | |
|---|---|---|
| EP | 0905144 A1 | 3/1999 |
| EP | 1953174 A1 | 8/2008 |

(Continued)

OTHER PUBLICATIONS

S.P. Sanghvi, et al., "A method to control particle size of cellulose acetate trimellitate microspheres", J. Microencapsulation, vol. 10, No. 2, pp. 181-194 (1993).

Charles L. McCormick, et al., "Solution Studies of Cellulose in Lithium Chloride and N,N-Dimethylacetamide", Macromolecules, vol. 18, pp. 2394-2401 (1985).

Judy D. Timpa, "Application of Universal Calibration in Gel Permeation Chromatography for Molecular Weigh Determinations of Plant Cell Wall Polymers: CottonFiber", J. Agric. Food Chem., vol. 39, pp. 270-275 (1991).

Jürgen Röhrling, et al., "A Novel Method for the Determination of Carbonyl Groups in Cellulosics by Fluorescence Labeling. 2. Validation and Applications", Biomacromolecules, vol. 3, pp. 969-975 (2002).

(Continued)

Primary Examiner — Jeffrey T. Palenik

(57) ABSTRACT

A microsphere is claimed which includes at least one biodegradable polymer and at least one local anesthetic, wherein about 75% of the at least one local anesthetic is released by about 72 hours and from about 80% to about 90% of the at least one local anesthetic is released by about 120 hours, thereby relieving chronic pain for at least 28 days.

15 Claims, 8 Drawing Sheets

(56) References Cited

U.S. PATENT DOCUMENTS

| | | | |
|---|---|---|---|
| 8,152,777 | B2 | 4/2012 | Campbell et al. |
| 9,505,062 | B2 | 11/2016 | Hielscher et al. |
| 2002/0086990 | A1 | 7/2002 | Kumar et al. |
| 2002/0114835 | A1 | 8/2002 | Sackler et al. |
| 2003/0078209 | A1 | 4/2003 | Schmidt |
| 2003/0152637 | A1* | 8/2003 | Chasin ............... A61K 9/0024 424/501 |
| 2005/0131225 | A1 | 6/2005 | Kumar et al. |
| 2005/0154093 | A1 | 7/2005 | Kwon et al. |
| 2006/0008505 | A1 | 1/2006 | Brandon |
| 2006/0093672 | A1 | 5/2006 | Kumar et al. |
| 2006/0121266 | A1 | 6/2006 | Fandel et al. |
| 2007/0054880 | A1 | 3/2007 | Saferstein et al. |
| 2007/0213522 | A1 | 9/2007 | Harris et al. |
| 2007/0237741 | A1 | 10/2007 | Figuly et al. |
| 2007/0237742 | A1 | 10/2007 | Figuly et al. |
| 2008/0164440 | A1 | 7/2008 | Maase et al. |
| 2008/0194805 | A1 | 8/2008 | Vignon et al. |
| 2008/0214695 | A1 | 9/2008 | Pathak et al. |
| 2009/0220560 | A1 | 9/2009 | Wan et al. |
| 2009/0263441 | A1 | 10/2009 | McKay |
| 2010/0065660 | A1 | 3/2010 | Hull et al. |
| 2010/0096481 | A1 | 4/2010 | Hull et al. |
| 2010/0203151 | A1 | 8/2010 | Hiraoka |
| 2011/0081422 | A1 | 4/2011 | Lynch et al. |
| 2011/0082427 | A1 | 4/2011 | Golzarian et al. |
| 2011/0089375 | A1 | 4/2011 | Chan et al. |
| 2011/0293690 | A1 | 12/2011 | Griffin et al. |
| 2012/0156289 | A1 | 6/2012 | Blaskovich et al. |
| 2014/0199381 | A1 | 7/2014 | Ying et al. |

FOREIGN PATENT DOCUMENTS

| | | | |
|---|---|---|---|
| EP | 2022802 | A1 | 2/2009 |
| EP | 2614843 | A2 | 7/2013 |
| GB | 2055107 | A | 2/1981 |
| JP | 60214728 | A | 10/1985 |
| JP | 6228011 | B2 | 8/1994 |
| JP | 11504634 | | 5/1996 |
| JP | 8277216 | | 10/1996 |
| JP | 11511763 | | 10/1999 |
| JP | 2002509107 | A | 3/2002 |
| JP | 2011503213 | A | 1/2011 |
| WO | 9634599 | A1 | 11/1996 |
| WO | 9749391 | A1 | 12/1997 |
| WO | 9856894 | A1 | 12/1998 |
| WO | 9936071 | A1 | 7/1999 |
| WO | 2002053599 | A2 | 7/2002 |
| WO | 2003068245 | A1 | 8/2003 |
| WO | 2005047339 | A1 | 5/2005 |
| WO | 2005058198 | A1 | 6/2005 |
| WO | 2006006140 | A1 | 1/2006 |
| WO | 2007106251 | A1 | 9/2007 |
| WO | 2007140573 | A1 | 12/2007 |
| WO | 2009021688 | A1 | 2/2009 |
| WO | 2009067462 | A1 | 5/2009 |
| WO | 2010/118285 | A1 | 10/2010 |
| WO | 2010120269 | A1 | 10/2010 |
| WO | 2012034049 | A2 | 3/2012 |
| WO | 2012045094 | A1 | 4/2012 |
| WO | 2013/003619 | A1 | 1/2013 |
| WO | 2015164272 | A2 | 10/2015 |

OTHER PUBLICATIONS

Matija Strlic, et al., "Size exclusion chromatography of cellulose in LiCl/N,N-dimethylacetamide", J. Biochem. Biophys. Methods, vol. 56, pp. 265-279 (2003).
Tatyana Ecrmeeva, "Size-exclusion chromatography of enzymatically treated cellulose and related polysaccharides: a review", J. Biochem. Biophys. Methods, vol. 56, pp. 253-264 (2003).
Yen T. Bao, et al., "New Approach to Aqueous Gel Permeation Chromatography of Nonderivatized Cellulose", Journal of Applied Polymer Science, vol. 25, pp. 263-275 (1980).
Matija Strlic, et al., "Evaluation of size-exclusion chromatography and viscometry for the determination of molecular masses of oxidised cellulose", Journal of Chromatography A, vol. 805, pp. 93-99 (1998).
Ute Henniges, et al., "Studies into the Early Degradation Stages of Cellulose by Different Iron Gall Ink Components," Macromol. Symp., vol. 262, pp. 150-162 (2008).
Akira Isogai, et al., "Preparation of polyuronic acid from cellulose by TEMPO-mediated oxidation", Cellulose, vol. 5, pp. 153-164 (1998).
Tsuguyuki Saito, et al., "TEMPO-mediated oxidation of native celulose: SEC-MALLS analysis of water-soluble and -insoluble fractions in the oxidized products", Cellulose, vol. 12, pp. 305-315 (2005).
Arne Lund Kvernheim, et al., "Size-Exclusion Chromatography and Methylation Analysis of Cellulose in N,N-Dimethylacetamide/ LiCl", Acta Chem. Scand., vol. 43, pp. 209-211 (1989).
Izumi Shibata, et al., "Nitroxide-mediated oxidation of cellulose using TEMPO derivatives: HPSEC and NMR analyses of the oxidized products", Cellulose, vol. 10, pp. 335-341 (2003).
Yoshihiro Shigemasa, et al., "Ruthenium Catalyzed Oxidation of Polysaccharide", Polymer Journal, vol. 23, No. 10, pp. 1279-1281 (1991).
M. Singh, et al., "An insulin delivery system from oxidized cellulose", Journal of Biomedical Materials Research, vol. 15, pp. 655-661 (1981).
Soroor Sharifpoor, et al., "In vitro release of a water-soluble agent from low viscosity biodegradable, injectable oligomers", European Journal of Pharmaceutics and Biopharmaceutics, vol. 65, pp. 336-345 (2007).
R. van Dijkhuizen-Radersma, et al., "Control of vitamin B12 release from poly(ethylene glycol)/poly(butylene brephthalate) multiblock copolymers", Biomaterials, vol. 23, pp. 1527-1536 (2002).
Akihiro Matsumoto, et al., "A novel preparation method for PLGA microspheres using non-halogenated solvents", Journal of Controlled Release, vol. 129, pp. 223-227 (2008).
Sergio Freitas, "Microencapsulation by solvent extraction/ evaporation: reviewing the state of the art of microsphere preparation process technology", Journal of Controlled Release, vol. 102, pp. 313-332 (2005).
Christian Wischke, et al., "Principles of encapsulating hydrophobic drugs in PLA/PLGA microparticles", International Journal of Pharmaceutics, vol. 364, pp. 298-327 (2008).
P. J. Watts, et al., "Microencapsulation Using Emulsification/ Solvent Evaporation: An Overview of Techniques and Applications", Critical Reviews in Therapeutic Drug Carrier Systems, vol. 7, Issue 3, pp. 235-259 (1990).
Andreas S. Lübbe, M.D., Ph.D., et al., "Clinical Applications of Magnetic Drug Targeting", Journal of Surgical Research, vol. 95, pp. 200-206 (2001).
Brian Dennis Plouffe, "Magnetic particle based microfluidic separation of cancer cells from whole blood for applications in diagnostic medicine", Chemical Engineering Dissertations, Northeastern University (2011).
R.V. Ramanujan, et al., "Magnetic Particles for Hyperthermia Treatment of Cancer", Proc. First Intl. Bioengg. Conf., 69-72 (2004).
Barbara D. Raynal, "Nano-Magnetic Particles for Cancer Diagnostics", Biological Applications, The 2009 NNIN REU Research Accomplshments, pp. 32-33 (2009).
Margarethe Hofmann-Amtenbrink, et al., "Superparagmagnetic nanoparticles for biomedical applications", Transworld Research Network, vol. 37/661, No. 2, pp. 119-149 (2009).
J.F.W. Nijsen, et al., "General introduction: Advances in nuclear oncology, microspheres for internal radionuclide therapy of liver tumours", Current Medicinal Chemistry, vol. 9, No. 1, pp. 73-82 (2002).
S. Ho, et al., "Clinical evaluation of the partition model for estimating radiation doses from yttrium-90 microspheres in the treatment of hepatic cancer", European Journal of Nuclear Medicine, vol. 24, No. 3, pp. 293-298 (1997).

(56) References Cited

OTHER PUBLICATIONS

Russell J. Mumper, et. al., "Neutron-Activated Holmium-166-poly (L-Lactic Acid) Microspheres: A Potential Agent for the Internal Radiation Therapy of Hepatic Tumors", The Journal of Nuclear Medicine, vol. 32, No. 11, pp. 2139-2143 (1991).
S. Ho, et al., "Internal Radiation Therapy for Patients with Primary or Metastatic Hepatic Cancer", Cancer, vol. 83, No. 9, pp. 1894-1907 (1998).
J.H. Turner, et al., "Ho-microsphere liver radiotherahpy: a preclinical SPECT dosimetry study in the pig", Nuclear Medicine Communications, vol. 15, pp. 545-553 (1994).
A. Jaworek, "Electrospray droplet sources for thin film deposition", J Mater Sci, vol. 42, pp. 266-297 (2007).
A. Jaworek, et al., "Trajectories of charged aerosol particles near a spherical collector", Journal of Electrostatics, vols. 51-52, pp. 603-609 (2001).
Robert Moerman, et al., "Minaturized Electrospraying as a Technique for the Production of Microarays of Reproducible Micrometer-Sized Protein Spots", Anal. Chem., vol. 73, pp. 2183-2189 (2001).
James C. Andrews, et al., "Hepatic Radioembolization with Yttrium-90 Containing Glass Microspheres: Preliminary Results and Clinical Follow-Up", The Journal of Nuclear Medicine, vol. 35, No. 10, pp. 1637-1644 (1994).
International Search Report from European Application No. EP 13170166.6 dated Aug. 6, 2013.
International Search Report from European Application No. 13174367.6 dated Sep. 16, 2013.
International Search Report from European Application No. 13174376.7 dated Sep. 25, 2013.
Extended European Search Report from Appl. No. EP 13174412.0 dated Nov. 6, 2011.
International Search Report from Application No. PCT/US2012/044692 dated Jan. 7, 2014.
International Search Report from PCT Appl. No. PCT/US13/60123 dated Apr. 28, 2014.
Mccormick et al., Solution studies of cellulose in lithium chloride and N, N-dimethylacetamide, Macromolecules, vol. 18, No. 12, Dec. 1, 1985, pp. 2394-2401.
Kim et al., "Structural studies of electrospun cellulose nanofibers", Polymer, Elsevier Science Publishers B.V. BG, vol. 47, No. 14, Jun. 28, 2006, pp. 5097-5107.
Extended European Search Report for application No. 15186802 dated Feb. 1, 2016.
Le Corre P et al: "Preparation and characterization of bupivacaine-loaded polylactide and polylactide-co-glycolide microspheres", International Journal of Pharmaceutics, Elsevier BV, NL, vol. 107, No. 1, Jun. 20, 1994, pp. 41-49.
Brown et al., "Solvent'/Non-Solvent Sintering:: A Novel Route to Create Porous Microsphere Scaffolds for Tissue Regeneration", J Biomed Mater Res B Appl Biomater. Author manuscript; Oct 1, 2009, pp. 1-21.
Castillo et al., "Glucocorticoids Prolong Rat Sciatic Nerve Blockade In Vivo From Bupivacaine Microspheres," Anesthesiology, Nov. 1996, vol. 85(5), pp. 1157-1166, 1164.
Chahar et al., "Liposomal bupivacaine: a review of a new bupivacaine formulation", Journal of Pain Research, 2012, pp. 257-264.
Hu et al., "Pharmacokinetic Profile of Liposome Bupivacaine Injection Following a Single Administration at the Surgical Site", Clinical Drug Investigation ,2013, vol. 33:, pp. 109-115.
Cai et al., "Porous microsphere and its applciations", International Journal of Nanomedicine 2013, vol. 8, pp. 1111-1120.
Lambrechts et al., "Liposomal extended-release bupivacaine for postsurgical analgesia", Patient Preference and Adherence 2013, vol. 7, pp. 885-890.
McDonald et al., "Determination of Local Tissue Concentrations of Bupivacaine Released From Biodegradable Microspheres and the Effect of Vasoactive Compounds on Bupivacaine Tissue Clearance Studied by Microdialysis Sampling," Pharmaceutical Research, Nov. 19, 2002, vol. 19(11), pp. 1745-1752.
Ghanbar et al., "Preparation of porous microsphere-scaffolds by electrohydrodynamic forming and thermally induced phase separation", Materials Science and Engineering, 2013, vol. C33, pp. 2488-2498.
Davidson, et al., "High-Dose Bupivacaine Remotely Loaded into Multivesicular Liposomes Demonstrates Slow Drug Release Without Systemic Toxic Plasma Concentrations After Subcutaneous Administration in Humans", Anesthetic Pharmacology and Preclinical Pharmacology, Apr. 2010, vol. 110, No. 4, pp. 1018-1023.
Jiang et al., Preparation of novel porous starch microsphere foam for loading and release of poorly water soluble drug:, Drug Dev Ind Pharm, 2014; vol. 40(2), pp. 252-259.
Strichartz et al., "Mitigation of Experimental, Chronic Post-Thoracotomy Pain by Preoperative Infiltration of Local Slow-Release Bupivacaine Microspheres", International Anesthesia Research Society, Jun. 2015, vol. 120, No. 6, pp. 1375-1384.
Mogensen et al., "The Roles of Acute and Chronic Pain in Regression of Sensory Analgesia During Continuous Epidural Bupivacaine Infusion," Anesthesia and Analgesia, Aug. 1988, vol. 67(8), pp. 737-740.
Ohri et al., "Prolonged Nerve Block by Microencapsulated Bupivacaine Prevents Acute Postoperative Pain in Rats", Regional Anesthesia and Pain Medicine, vol. 37, No. 6, Nov.-Dec. 2012, pp. 607-615.
Ohri, et al., "Inhibition by Local Bupivacaine-Releasing Microspheres of Acute Postoperative Pain from Hairy Skin Incision:", Pain and Analgesic Mechanisms, Sep. 2013, vol. 117 , No. 3, pp. 717-730.
Paganelli et al., "Actions of Bupivacaine, A Widely Used Local Anesthetic, On NMDA Receptor Responses," The Journal of Neuroscience, Jan. 14, 2015, vol. 35(2), pp. 831-842.
Schmidt et al., "Local Pathology and Systemic Serum Bupivacaine After Subcutaneous Delivery of Slow-Releasing Bupivacaine Microspheres," Anesthesia and Analgesia, Jan. 2015, vol. 120(1), pp. 36-44.
Tong et al., "Liposomal bupivacaine and clinical outcomes", Best Practice & Research Clinical Anaesthesiology, 2014, vol. 28, pp. 15-27.
Deer et al., "Intrathecal Bupivacaine for Chronic Pain: A Review of Current Knowledge. Neuromodulation," International Neuromodulation Society, Nov. 4, 2002, vol. 5(4), pp. 196-207.
Andreae, et al., "Local anaesthetics and regional anaestesia for preventing chronic pain after surgery (Review)", The Cochrane Library 2012, Issue 10, pp. 1-96.
Drager, "Studies on the Regional Long-Term Anesthesia With Bupivacaine-Dexamethasone-Polymer Microspheres: Application for the Surgery and Possible Mechanism of Action of Glucocorticoids," Dissertation Winter Semester, 1998.).
Viscusi et al., "The Pharmacokinetics and Pharmacodynamics of Liposome Bupivacaine Administered via a Single Epidural Injection to Healthy Volunteers, Regional Anesthesia and Pain Medicine," vol. 37, No. 6, Nov.-Dec. 2012 pp. 616-622.
Kopacz et al., "A Model to Evaluate the Pharmocokinetic and Pharmacodynamic Variables of Extended-Release Productds Using In Vivo Tissue Microdialysis in Humans: Bupivacaine-Loaded Micropasules", Anesth. Analog. 200, vol. 97, pp. 124-131.
Kopacz et al., "The Dose Response and Effects of Dexamethasone on Bupivacaine Microcapsules for Intercostal Blockade (T9 to T11) in Healthy Volunteers," Anesth. Analog, 2003, vol. 96, pp. 576-582.
Pedersen et al., "Bupivacaine in Microcapsules Prolongs Analgesia After Subcutaneous Infiltration in Humans: A Dose-Finding Study," Anesth Analog, 2004, vol. 99, pp. 912-918.
Curley et al., "Prolonged Regional Nerve Blockade", Anesthesiology, Jun. 1996, vol. 84, pp. 1401-1410.
Bayman et al. "A Prospective Study of Chronic Pain after Thoracic Surgery," Anesthesiology, vol. 126, No. 5 (2017).
Bong et al. "Effects of Preemptive Epidural Analgesia on Post-thoracotomy Pain," Journal of Cardiothoracic and Vascular Anesthesia, vol. 19, No. 6, pp. 786-793 (2005).
Greene, "Chronic Pain: Pathology and Treatment Implications," Topics in Companion Animal Medicine, vol. 25, No. 1, pp. 5-9, 6, Feb. 2010.
Ju etl al., "Comparison of Epidural Analgesia and Intercostal Nerve Cryoanalgesia for Post-Thoracotomy Pain Control," European Journal of Pain, vol. 12 (2008) pp. 378-384.

(56) References Cited

OTHER PUBLICATIONS

Santamaria et al., "Drug Delivery Systems for Prolonged Duration Local Anesthesia," Materials Today, p. 1, Dec. 2016.
Song et al., "Incidence of Post-Thoracotomy Pain: A Comparison Between Totalintravenous Anaesthesia and Inhalation Anaesthesia," European Journal of Cardio-Thoracic Surgery, vol. 41 pp. 1078-1082 (2012).
Suter et al. "Development of Neuropathic Pain in the Rat Spared Nerve Injury Model is not Prevented by a Peripheral Nerve Block," Anesthesiology, vol. 99, No. 6, pp. 1402-1408, (2003).
Yanagidate and Strichartz, "Bupivacaine Inhibits Activation of Neuronal Spinal Extracellular Receptor-activated Kinase through Selective Effects on Ionotropic Receptors," Anesthesiology, vol. 104, No. 4, Apr. 2006, pp. 805-814.
European Search Report dated Dec. 5, 2017 issued in corresponding European Appln. No. 15186802.3.
Japanese Office Action dated Apr. 18, 2019 issued in corresponding JP Appln. No. 2015-188019.

\* cited by examiner

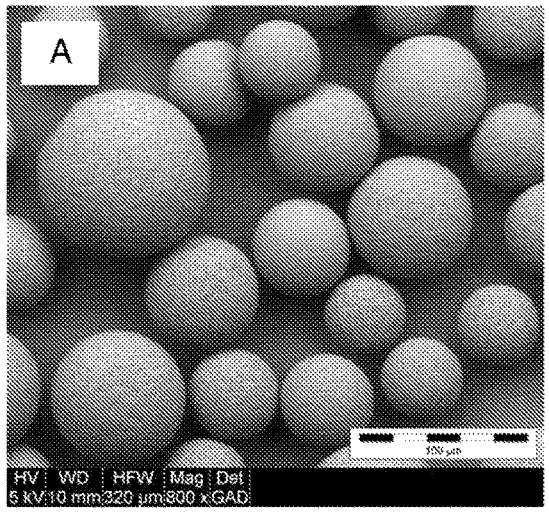
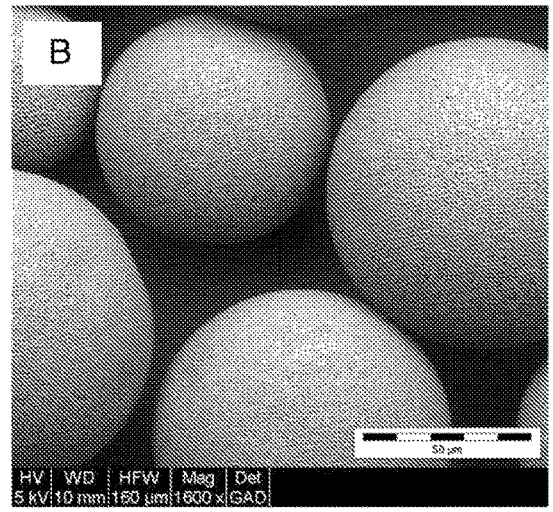
FIG. 1A
FIG. 1B
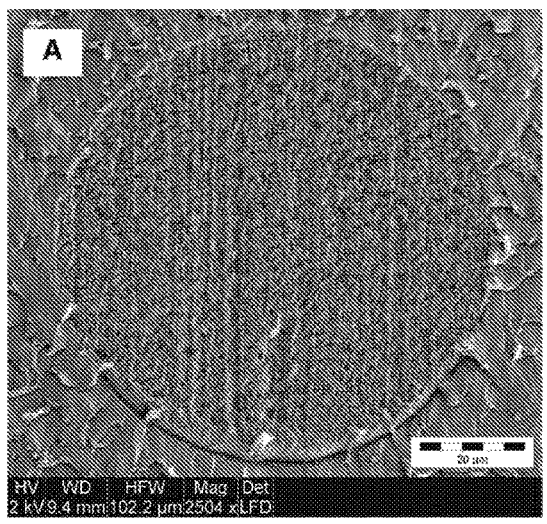
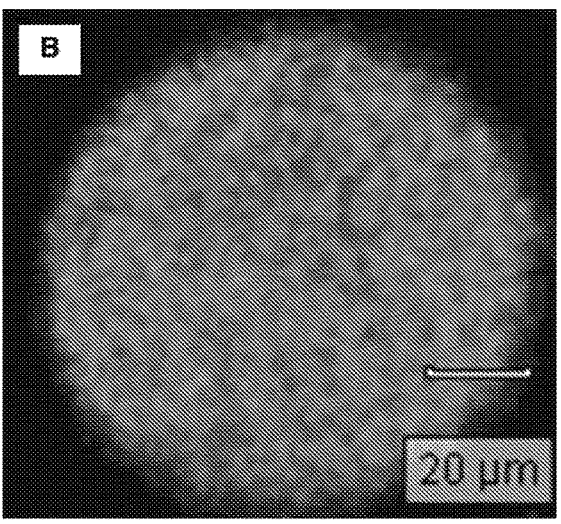
FIG. 2A
FIG. 2B

DRUG LOADED MICROSPHERES FOR POST-OPERATIVE CHRONIC PAIN

CROSS-REFERENCE TO RELATED APPLICATIONS

This application claims the benefit of and priority to U.S. Provisional Patent Application No. 62/056,129, filed Sep. 26, 2014, the entire disclosure of which is incorporated by reference herein.

BACKGROUND

Technical Field

The present disclosure relates to pharmaceuticals, compositions, drug-device combination products, and methods for treating medical conditions. In embodiments, compositions of the present disclosure may be used to treat chronic postoperative pain. In embodiments, the present disclosure relates to optimized pain management as a function of dosage and release kinetics of local anesthetics from implantable biodegradable microspheres.

Background of Related Art

Postoperative pain lasting for more than several days and even weeks affects many patients. For example, chronic pain following thoracotomy occurs at rest, e.g., with shallow breathing, and also has a pronounced movement-related component during coughing, stretching or twisting, e.g., mechano-hyperalgesia. While a variety of local and other anesthetic methods have been shown to reduce postoperative pain, the mechanisms of effect in chronic pain, unlike acute pain, are not well-understood since such drugs are known to act on multiple different targets.

Local anesthetics have previously been used perioperatively to reduce acute pain. Although peripheral nerve blocks, epidurals, and spinal anesthetics usually produce numbness for about 4 to about 12 hours, they are ineffective for long duration. Several other treatment strategies have also been employed, including continuous infusion of local anesthetics, e.g., through a catheter placed in the wound, and a variety of materials that slowly release drug(s) into tissue around the wound. Suitable delivery materials include multivesicular lipid suspensions, (e.g., EXPAREL®, a liposomal sustained-release bupivacaine formulation from Pacira Pharmaceuticals, Inc., San Diego, Calif.), bone waxes, biodegradable polymers, e.g., poly(lactic-co-glycolic acid) ("PLGA") and other materials. Microspheres formed from biodegradable materials containing local anesthetic compositions are also known and have been used to treat acute postoperative pain (e.g., PLGA, such as those from Purdue Pharmaceuticals originally developed out of the Langer-Berde collaboration between MIT and Boston Children's Hospital). However, there is no information, data, or opinion in the public domain that would suggest any impact on chronic pain from these sustained-release formulations of bupivacaine.

There has been a lack of published information regarding the optimization of drug dosing and drug release kinetics of local anesthetics in treating chronic postoperative pain. Improved drug delivery compositions, including those suitable for treating chronic pain, remain desirable.

SUMMARY

According to one embodiment of the present disclosure a microsphere is provided. The microsphere includes at least one biodegradable polymer and at least one local anesthetic, wherein about 75% of the at least one local anesthetic is released by about 72 hours and from about 80% to about 90% of the at least one local anesthetic is released by about 120 hours, thereby relieving chronic pain for at least 28 days.

According to another embodiment of the present disclosure a microsphere is provided. The microsphere includes at least one biodegradable polymer and at least one local anesthetic, wherein the at least one local anesthetic is released substantially linearly for approximately first 120 hours, thereby relieving chronic pain for at least 28 days.

According to one aspect of the above embodiments, the at least one local anesthetic is present in amount of about 60% by weight of the microsphere. The at least one local anesthetic may include one or more of the following: lidocaine, procaine, cocaine, benzocaine, bupivacaine, mepivacaine, prilocaine, articaine, tetracaine, dibucaine, chloroprocaine, etidocaine, oxybuprocaine, cocaethylene,dimethocaine, butacaine, proparacaine hydrochloride, proparacaine,piperocaine, hexylcaine, fluorescein, proparacaine, and combinations thereof According to another aspect of the above embodiments, the at least one local anesthetic is bupivacaine.

According to a further aspect of the above embodiments, the at least one biodegradable polymer is poly(lactic-co-glycolic acid). The poly(lactic-co-glycolic acid) may include polylactic acid and glycolic acid at a ratio of about 75:25.

According to one aspect of the above embodiments, the microsphere includes a shell having a porosity from about 1% to about 60% of a surface area of the microsphere.

According to a further embodiment of the present disclosure, a method for treating chronic pain is disclosed. The method includes: implanting at least one microsphere at a treatment site, the microsphere including: at least one biodegradable polymer and at least one local anesthetic, wherein about 75% of the at least one local anesthetic is released by about 72 hours and from about 80% to about 90% of the at least one local anesthetic is released by about 120 hours, thereby relieving chronic pain for at least 28 days.

According to one aspect of the above embodiment, the at least one microsphere is implanted preoperatively or postoperatively.

According to another aspect of the above embodiment, the method further includes forming a suspension including the at least one microsphere.

According to a further aspect of the above embodiment, the method further includes injecting the suspension into the treatment site.

According to one aspect of the above embodiment, the method further includes depositing the suspension on at least a portion of a medical device to form a film thereon, the film including the at least one microsphere particle.

BRIEF DESCRIPTION OF DRAWINGS

Various embodiments of the present disclosure will be described herein below with reference to the figures wherein:

FIGS. 1A-B are scanning electron microscope images of poly(lactic-co-glycolic acid) microspheres encapsulating bupivacaine in accordance with the present disclosure;

FIG. 2A is a scanning electron microscope image of a cross-sectioned microsphere of FIG. 1A in accordance with the present disclosure;

FIG. 2B is a Raman spectroscopy image of a cross-sectioned microsphere of FIG. 1A in accordance with the present disclosure;

DETAILED DESCRIPTION OF THE EMBODIMENTS

Figure 3:
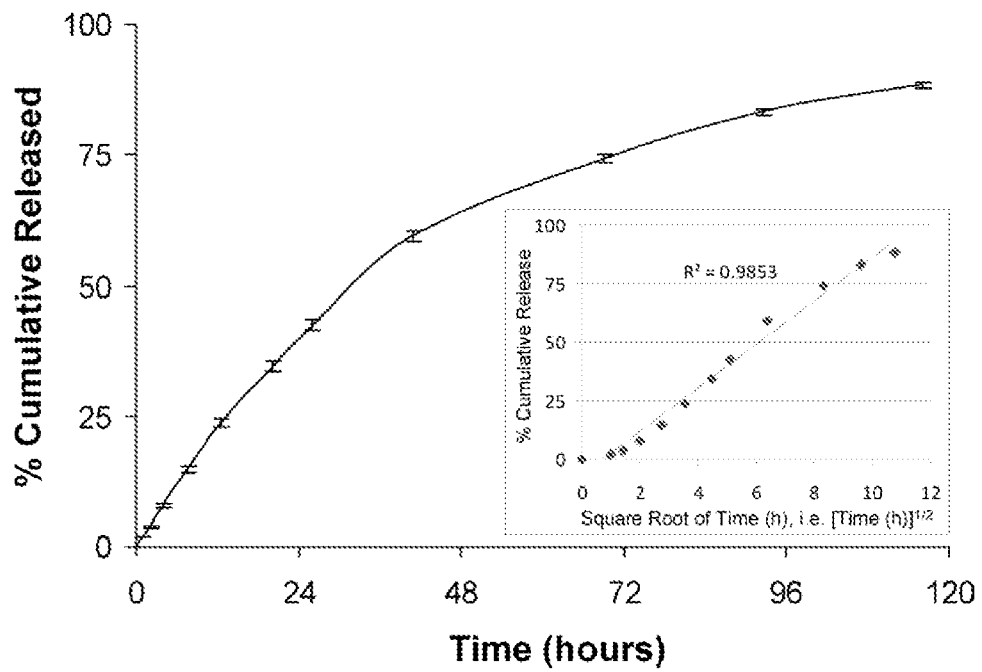
FIG. 3 is a plot of bupivacaine in vitro release profile of the microspheres of FIGS. 1A-B in accordance with the present disclosure.

The present disclosure provides pharmaceuticals, compositions, drug-device combination products, and methods for preventing/treating pain. The compositions include microspheres formed from a biodegradable polymer encapsulating a bioactive agent, e.g., a local anesthetic. Although various embodiments of the present disclosure are specific to microspheres, the disclosure is also applicable to any macro, micro, or nano capsules, spheres, or any other particles having any regular or irregular shape and size from about 0.001 micrometers to about 1,000 micrometers, in embodiments from about 0.01 micrometers to about 500 micrometers.

Microspheres may be formed using any suitable liquid-in-liquid (e.g., oil-in-oil, water-in-oil, oil-in-water, etc.) extraction method. In embodiments, microspheres may be formed by using an emulsion method followed by a solvent extraction step in extraction media.

As used herein, the term "emulsion" refers to a mixture of two or more liquids that are immiscible, in which one liquid forms a continuous phase and the other liquid forms a discontinuous phase.

The terms "discontinuous phase" and "disperse phase" are used interchangeably and refer to a compound being dispersed through the continuous phase and may include the local anesthetic, as well as any encapsulating biodegradable polymer and/or corresponding solvent or solvating agent.

As used herein the term "continuous phase" refers to a liquid, such as oils, that are used to extract any solvent or solvating agent from the discontinuous phase. These liquids are usually immiscible with the solvent employed in the discontinuous phase.

As used herein the terms "thinning agent phase" and "third phase" are used interchangeably and refer to a liquid that reduces the viscosity of the continuous phase, is miscible with the continuous phase and/or removes residual continuous phase from the surface of the microsphere(s). In embodiments, the thinning agent may be immiscible with the discontinuous phase.

Microspheres according to the present disclosure may be formed using an oil-in-water emulsification process described above. The solution may include any suitable biodegradable polymer, solvent, local anesthetic, optional emulsifier, and/or surfactant. In embodiments, additional bioactive agents may be included, which may be the same or different from the local anesthetic included in the microspheres.

Suitable biodegradable polymers used to form microspheres according to the present disclosure include, but are not limited to, aliphatic polyesters, polyamides, polyamines, polyalkylene oxalates, poly(anhydrides), polyamidoesters, copoly(ether-esters), poly(carbonates) including tyrosine derived carbonates, poly(hydroxyalkanoates) such as poly (hydroxybutyric acid), poly(hydroxyvaleric acid), and poly (hydroxybutyrate), polyimide carbonates, poly(imino carbonates) such as such as poly(bisphenol A-iminocarbonate), polyorthoesters, polyoxaesters including those containing amine groups, polyphosphazenes, poly(propylene fumarates), polyurethanes, polymer drugs such as polydiflunisal, polyaspirin, and protein therapeutics, biologically modified (e.g., protein, peptide) bioabsorbable polymers, and copolymers, block copolymers, homopolymers, blends, and combinations thereof.

In embodiments, suitable polymers used to form microspheres include aliphatic polyesters such as, but not limited to, polylactide, polylactide-co-glycolide, polylactide-polycaprolactone, homopolymers and copolymers of lactide (including lactic acid, D-,L- and meso lactide), glycolide (including glycolic acid), epsilon-caprolactone, p-dioxanone (1,4-dioxan-2-one), trimethylene carbonate (1,3-dioxan-2-one), alkyl derivatives of trimethylene carbonate, Δ-valero-lactone, β-butyrolactone, γ-butyrolactone, ε-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one, 2,5-diketomorpholine, pivalolactone, α,α-diethylpropiolactone, ethylene carbonate, ethylene oxalate, 3-methyl-1,4-dioxane-2,5-dione, 3,3-diethyl-1,4-dioxan-2,5-dione, 6,8-dioxabicycloctane-7-one, and copolymers thereof as well as combinations thereof.

Suitable biodegradable polymers for forming microspheres according to the present disclosure may include poly (lactide-co-glycolide acid) ("PLGA") having polylactic acid ("PLA") and glycolic acid ("GA") at a ratio of about 50:50 to about 100:00, in embodiments, the ratio of PLA to GA may be about 75:25.

Suitable solvents for forming the biodegradable polymer solution include, but are not limited to, ethyl acetate, methylene chloride, perchloroethane, trichloroethylene, hexafluoroisopropanol (HFIP), chloroform, tetrahydrofuran, dimethyl formamide, as well as those pharmaceutical solvents listed in the ICH Q3C (International Conference on Harmonization—residual solvents used in pharmaceutical processing) and combinations thereof The optional emulsifier may be present in an amount from about 0.01% by weight and/or volume to about 25% by weight and/or volume of the solvent, in embodiments from about 0.1% by weight and/or volume to about 10% by weight and/or volume of the solvent, in further embodiments from about 0.5% by weight and/or volume to about 5% by weight and/or volume of the solvent. For oil-in-oil processes, the use of an emulsifier is optional. Suitable emulsifiers include, but are not limited to, water-soluble polymers, such as polyvinyl alcohol ("PVA"), polyvinyl pyrrolidone (PVP), polyethylene glycol (PEG), polypropylene glycol (PPG), PLURONICS™, TWEENS™, polysaccharides, phospholipids, and combinations thereof.

Suitable local anesthetics which may be included in accordance with the present disclosure include, but are not limited to, lidocaine, ropivacaine, procaine, cocaine, benzocaine, bupivacaine, mepivacaine, prilocaine, articaine, tetracaine, dibucaine, chloroprocaine, etidocaine, oxybuprocaine, cocaethylene,dimethocaine, butacaine, proparacaine hydrochloride, proparacaine,piperocaine, hexylcaine, fluorescein, proparacaine, and combinations thereof.

Biodegradable microspheres according to the present disclosure may have a theoretical local anesthetic loading from about 30% to about 85% by weight of the microspheres, in embodiments from about 45% to about 75%, in further embodiments from about 50% to about 70%, in additional embodiments from about 55% to about 65% by weight of the microspheres. Biodegradable microspheres may have an actual local anesthetic loading from about 25% to about 90%, in embodiments from about 40% to about 80%, in further embodiments from about 45% to about 75%, in additional embodiments from about 50% to about 70%. In further embodiments, microspheres according to the present disclosure may have an actual local anesthetic loading at about 60%.

In forming microspheres according to the present disclosure, one or more local anesthetics may be added to a solution of the biodegradable polymer, and are mixed sufficiently to ensure a uniform suspension or homogeneous solution (e.g., with an appropriate solvent such as methylene chloride, to be subsequently used in an oil-in-water emulsion/solvent evaporation process). Biodegradable polymer may be present in the solution in an amount from about 0.1% by weight to 50% by weight of the solution, in embodiments, from about 1.0% by weight to about 25% by weight of the solution, in embodiments from about 5% by weight to 15% by weight of the solution. The local anesthetic and biodegradable polymer solution forms the discontinuous phase, which is added drop-wise to a vessel including a liquid forming a continuous phase. The continuous phase liquid may be any suitable aqueous or organic, polar or non-polar compound that is immiscible with the polar solvents used in forming the biodegradable polymer solution. Conversely, if a non-polar solvent is used to dissolve the biodegradable polymer, the continuous phase liquid may be any polar compound that is immiscible with the non-polar solvent. The discontinuous phase liquid may be present in an amount from about 1% by volume to about 50% by volume of the continuous phase liquid, in embodiments from about 5% to about 20%.

The vessel possessing the continuous phase may be fitted with a baffle. The vessel may include a mixer with an impeller configured to rotate at a rate of from about 25 rpm to about 60,000 rpm, in embodiments, from about 100 rpm to about 15,000 rpm, in further embodiments from about 250 rpm to about 5,000 rpm. The stirring may continue from about 5 seconds to about 10 hours, in embodiments, from about 15 seconds to about 5 hours. The rate of rotation may be adjusted to obtain desired particle size. Size of the microspheres may be tailored by modulating the duration and the speed of homogenization (e.g., stirring of the discontinuous and continuous phases), temperature and/or pressure, altering the ratio of continuous to discontinuous phases, the shear rate, and the molecular weight and concentrations of the biodegradable polymer and/or the local anesthetic.

Upon completing the transfer of the discontinuous phase solution into the continuous phase, a third phase liquid may be added to the emulsion to remove the solvent from the discontinuous phase liquid. Suitable third phase liquids include any compound which is miscible with both the continuous and discontinuous phase liquids. The extraction of the solvent occurs due to the solvent being immiscible in the continuous phase liquid, but miscible in the third phase liquid. Suitable third phase liquids include isopropyl myristate, hexane, n-heptane, triglycerides and combinations thereof. The third phase liquid may be present in an amount from about 100% by volume to about 200% by volume of the continuous phase liquid, in embodiments from about 140% to about 150%.

Removal of the solvent from the continuous phase facilitates formation of microspheres including the local anesthetic encapsulated by the biodegradable polymer. The emulsion may be stirred from about 0.1 hour to about 24 hours, in embodiments from about 2 hours to about 5 hours, to aid in the extraction of the solvent from the microspheres. The microspheres may then be collected via filtration and washed (e.g., with aqueous or non-aqueous media) to remove any trace of continuous and discontinuous phase liquids on the surface of the microspheres. The microspheres may then be collected and transferred into a glass scintillation vial under a nitrogen or argon overlay. In embodiments, microspheres may also be formed using spray dry and jet mill techniques.

According to the present disclosure, biodegradable microspheres encapsulating the local anesthetic may be implanted locally to treat pain, such as chronic postoperative pain and/or hyperalgesia. Microspheres may be implanted by injection of a suspension including the microspheres using a syringe, a catheter, or any other intravenous medical device. The suspension may be formed at the time of use, immediately before injection, or at any other suitable time depending on the solution in which the microspheres are suspended and other factors. Microspheres may be implanted preoperatively, perioperatively, and/or postoperatively. Microspheres may be implanted at the treatment site and/or near nerves to relieve pain associated with nerve injury occurring during surgical procedures. In embodiments, microspheres according to the present disclosure may be used to perioperatively treat postoperative chronic pain associated with any surgical procedure, including, but not limited to, herniorraphy, thoracotomy, joint arthroscopy.

In other embodiments, the microspheres may be included in other implantable medical devices. Suitable medical devices may be any surgical implant, such as meshes, scaffolds, grafts, stents, sutures, patches, slings, buttresses, scaffolds, pledgets, and, in general, soft tissue repair devices, surgical prostheses and artificial organs; or may be topically applied medical products, such as wound dressings, coverings, tapes, gauzes, and the like, that can be used in medical/surgical procedures.

The microspheres may be applied to the medical devices as a film or coating. In embodiments, microsphere films may be cast directly from a microsphere suspension directly onto the medical devices in a single process step, thereby avoiding resuspension of microspheres to form homogenous suspensions suitable for coating medical devices. The film containing microsphere particles may be formed in a homogenous suspension (e.g., emulsion) of at least one biodegradable polymer and at least one solvent. Suitable polymers and solvents for forming the homogenous suspension include any polymers and solvents described above as suitable for forming microspheres according to the present disclosure.

Microspheres according to the present disclosure are particularly effective for treating chronic pain due to the distribution of bioactive agent and polymer, as well as surface morphology resulting in surface-erosion based release of the bioactive agent from the microspheres. Microspheres may have a mean diameter from about 0.001 micrometers to about 1,000 micrometers, in embodiments from about 0.1 micrometers to about 500 micrometers, in further embodiments from about 1 micrometers to about 250 micrometers, in additional embodiments from about 10 micrometers to about 150 micrometers, in yet further embodiments from about 55 micrometers to about 85 micrometers.

The relative polymer/local anesthetic distribution in the microspheres according to the present disclosure and their density may be wholly or partially uniform, e.g., including micro-domains. The porosity microspheres may be from about 0.0001% to about 33% of the volume of the microspheres, in embodiments from 0.001% to about 25% of the volume of the microspheres, in further embodiments from 0.01% to about 20% of the volume of the microspheres, in additional embodiments from 0.1% to about 15% of the volume of the microspheres. The microspheres may be fully spherical, partially spherical, or non-spherical.

The release-profile of the microspheres includes little or no initial burst, with relatively constant rate of release for about the first 48 hours, and a gradually declining rate of release from about 48 hours to about 120 hours, such that about 75% of the cumulative release of the local anesthetic occurs approximately within the first 72 hours and from about 80% to about 90% of the cumulative release occurs after about 120 hours.

An initial release burst may be from about 0% to about 25% in the first 10 seconds to about 10 minutes, in embodiments from about 1% to about 15% in the first 1 minute to about 8 minutes, in further embodiments from about 2% to about 10% in the first 2 minutes to about 7 minutes, and in additional embodiments from about 3% to about 5% in about first 5 minutes.

Approximately 75% of the cumulative release may occur from about 12 hours to about 120 hours, in embodiments from about 24 hours to about 96 hours, in further embodiments from about 36 hours to about 84 hours. Approximately from about 80% to about 90% of the cumulative release may occur from about 72 hours to about 168 hours, in embodiments from about 96 hours to about 144 hours, in further embodiments from about 108 hours to about 132 hours.

Second derivative of the cumulative release rate over the first 120 hours may be from about 0.1% per hour to about 10% per hour, in embodiments, from about 0.5% to about 5% per hour, in further embodiments from about 1% per hour to about 3% per hour. The microspheres according to the present disclosure also release the local anesthetic in a linear release rate, with $R^2$ being from about 0.94 to about 0.99, in embodiments $R^2$ may be about 0.985, when percent of the local anesthetic is plotted versus a square root of time as shown in FIG. 3 and described in further detail below.

It is believed that the release kinetics of the local anesthetics are important parameters for treating chronic post-operative hyperalgesia. The reason for this is that too fast a rate of release expends all of the local anesthetic in a short time, which is then locally metabolized or absorbed by the local vasculature and distributed to the general circulation, from which it is metabolized primarily hepatically, and then excreted. Rapid delivery also quickly exhausts the local anesthetic pool, leaving little or none to affect later anesthesia and also resulting in potentially toxic systemic concentrations.

In contrast, too slow a release rate prevents entry of the local anesthetic into the targeted tissue at a concentration sufficient for neural blockade; the local anesthetic may be removed from the deposited microspheres without ever achieving a functional blockade. Therefore, an optimal rate of release and duration of release is recommended, tailored to the specific requirements, which depend on the specific local anesthetic and its formulation pH, local anatomy of the target tissue, surface to volume relationships of the formulation, vascular richness, and other factors.

The microspheres also affect post-operative chronic pain for a period from about 1 day to about 35 days, in embodiments until about 28 days. It is believed that the effectiveness of the microspheres according to the present disclosure for treating chronic pain is due to the inhibition by the local of ionic sodium channels in local neurons. This conclusion is reached based on pharmacokinetic and systemic concentration as measured in the serum, as described in further detail in the Examples Section below.

Although it is generally well-accepted that impacting post-operative acute pain can favorably impact post-operative chronic pain, the extent and duration of this impact and the corresponding attributes of the sustained release anesthetic formulation are non-obvious. Several previous sustained-release formulations of bupivacaine, although impactful on acute pain have not been reported to impact chronic pain.

Although various embodiments of the present disclosure are specific to microspheres including a local anesthetic, the disclosure is also applicable to encapsulation of additional bioactive agents. In embodiments, as noted above, one or more bioactive agents may be added to the solvent such that the bioactive agents are incorporated into the biodegradable polymer solution, which may then be used to form various microspheres. It is also intended that combinations of bioactive agents may be used.

The following Examples are being submitted to illustrate embodiments of the present disclosure. These Examples are intended to be illustrative only and are not intended to limit the scope of the present disclosure. Also, parts and percentages are by weight unless otherwise indicated. As used herein, "room temperature" or "ambient temperature" refers to a temperature from about 20° C. to about 25° C. Unless otherwise specified, the Examples were conducted at ambient temperature, pressure of about 1 atmosphere.

EXAMPLES

Example 1

This Example describes formation of 60% by weight bupivacaine loaded poly (lactide-co-glycolide acid) (PLGA) microspheres.

About 0.16 grams of PLGA polymer dissolved per milliliter of Methylene Chloride (PLGA LACTEL® polymer having polylactic acid ("PLA") and glycolic acid ("GA") at a ratio of about 75:25) obtained from Durect Corp. (Pelham, Ala.) along with about 0.24 grams of bupivacaine (BASF, Chicago, Ill.) dissolved per milliliter of methylene chloride (Spectrum Chemicals, New Brunswick, N.J.) to form a solution. The solution was then subjected to a modified oil-in-water (o/w) emulsion/solvent evaporation technique with poly vinyl alcohol (PVA) being used as the emulsifier to form microspheres.

Microsphere size fractionation was achieved using differential sieving. Bupivacaine microspheres were wet-sieved into their respective size fractions using stainless-steel US Standard (ASTM E-11) testing sieves, 8 inches in diameter (W. S. Tyler, Mentor, Ohio). Three sieves were stacked in descending order, of about 150, 105, and 45 micrometers. Following solvent evaporation, the continuous phase containing the bupivacaine microspheres was poured through the top sieve and carefully washed with pressurized deionized water at about 90 pounds per inch$^2$ with a handheld sprayer to hydrodynamically drive smaller-diameter microspheres to the next sieve. The contents of each sieve were then collected under vacuum using Whatman No. 4 filter paper (Whatman Paper, Ltd, of GE Healthcare, Little Chalfont, UK) fitted in a Buchner funnel. The microspheres were allowed to air dry before storage under an argon overlay at about 4° C. After wet-sieving, microspheres of the size fraction from about 45 micrometers to about 105 micrometers were obtained having a mean particle size from about 5 micrometers to about 75 micrometers.

Following size fractionation, the microsphere batches were air dried overnight and stored under an argon overlay at about 4° C. Sterilization was carried out using JS8900 Batch Gamma Irradiator (Steris Isomedix Corp., Morton Grove, Ill.) to irradiate the sample using γ-irradiation at from about 11 kilograys ("kGy") to about 13 kGy.

About fifty milligrams of bupivacaine microspheres were dissolved in approximately 50 milliliters of acetonitrile, and then further diluted in about 10% by weight/volume acetonitrile in high-performance liquid chromatography ("HPLC") grade water. The resulting sample was then analyzed by an HPLC assay to yield the bupivacaine concentration. The percent drug loading was determined by calculating the total amount of bupivacaine in the starting sample, which was about 50 milligrams. The target percent drug loading was about 60% by weight of the microspheres, and the typical loading achieved was from about 55% by weight of the microspheres to about 60% by weight of the microspheres. Microspheres were uniformly spherical with a mean diameter of about 65 micrometers to about 75 micrometers, with standard deviation of about 10 micrometers to about 15 micrometers.

Collected bupivacaine microspheres were imaged using an FEI Quanta 600FEG environmental scanning electron microscope ("SEM") (FEI, Hillsboro, Oreg.). The bupivacaine microsphere specimens were mounted on carbon adhesive tape. To expose interior sections, some bupivacaine microspheres were cross-sectioned with a razor blade or mounted in epoxy and cross sectioned with a tungsten carbide microtome blade. The whole and cut specimens were imaged using low-vacuum and low-kilovolt conditions.

FIGS. 1A and 1B show SEM images of whole microspheres at about 800× and about 1600×, respectively. The SEM images show microspheres having uniform spherical geometry.

FIG. 2A shows an SEM of a cross-sectioned microsphere. The image showed the uniformly structured matrix within the microsphere. FIG. 2B shows a Raman microscopy chemical image of a cross-sectioned microsphere, demonstrating a uniform distribution of both bupivacaine and PLGA throughout the matrix. The PLGA and bupivacaine were identified by the colors cyan and magenta, respectively, which were interspersed throughout the cross-section. Scanning electron microscopy and Raman spectroscopy of FIGS. 2A and 2B, respectively, revealed a relatively uniform distribution of polymer and drug/active pharmaceutical ingredient (API) throughout the spheres, with no indication of bulk compartmentalization of either polymer or drug/API.

Gas physisorption isotherms (not shown) of the microspheres were also obtained, with the microspheres having a Brunauer-Emmett-Teller surface area of about 0.0834±0.0019 meters$^2$ per gram. For comparison, the theoretical surface area for microspheres having a diameter of about 70 micrometers with an assumed smooth surface would be about 0.0750 meters$^2$ per gram, based on the measured true density of 1.138±0.0009 grams per milliliter, a value not significantly below the measured surface area, therefore suggesting low porosity for the microspheres.

Release kinetics were measured in vitro in phosphate buffered saline ("PBS") at about 37° C. and results are plotted in the graph included as FIG. 3. The early rate of release in vitro was about 0.6 to about 0.75 milligrams per hour, from a suspension of about 100 milligrams of the bupivacaine microspheres per milliliter. The plot of FIG. 3 showed that release occurred at a near-constant rate for approximately the first 12 hours; about 50% of the total releasable bupivacaine was delivered by approximately 30 hours, and about 75% of the total releasable bupivacaine was delivered by about 72 hours. The release kinetics fit within the Higuchi model of diffusion-based, controlled-release systems. The linear plot of cumulative percent release versus the square root of time yielded an R$^2$ value of about 0.985.

Figure 4:
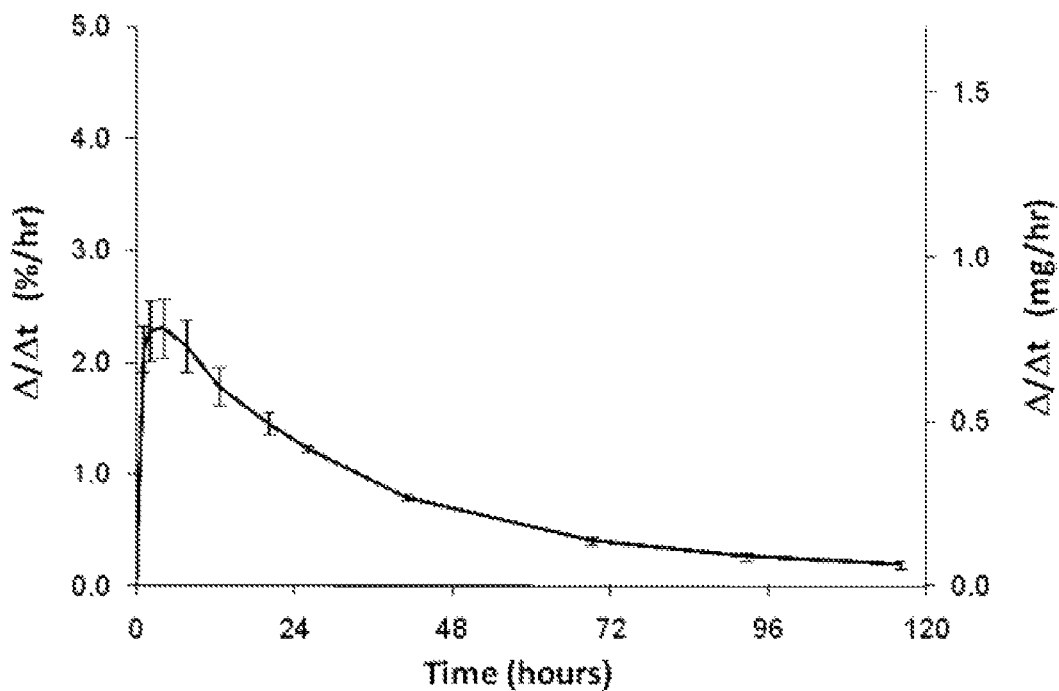
FIG. 4 is a plot of a first derivative of the release profile plot of FIG. 3 in accordance with the present disclosure.

FIG. 4 is a plot of a first derivative of the plot of the release profile of FIG. 3. The release rate was expressed in two different units on the y-axes, namely, percentage release per hour and milligrams per hour. The milligrams per hour values were calculated based on the actual total dose delivered per injection for the microspheres in the preclinical study, which was an average of about 34.0±1.0 milligrams per injection. The early rate of release varied from about 0.6 to 0.75 milligrams per hour for approximately the first 7 to 13 hours.

Example 2

This Example describes formation of placebo poly-lactide-co-glycolide (PLGA) microspheres.

The same process was followed as set forth in Example 1 above, except the placebo microspheres were prepared without bupivacaine.

Example 3

This Example describes implantation of microspheres of Example 1 and placebo microspheres of Example 2, the latter used as a negative control, into rats to determine effect of the presence of microspheres of Example 1.

A model for chronic post-operative hyperalgesia, induced by experimental thoracotomy in the rat, was used to examine the ability and duration of infiltrated microspheres of Example 1 to reduce chronic post-operative pain for approximately 4 weeks (about 28 days) after surgery. Microspheres of Example 1 were placed pre-operatively in the subcutaneous compartment surrounding an incision-retraction locus for experimental thoracotomy and reduction in prolonged hyperalgesia following thoracotomy was observed.

All procedures were in keeping with international standards for the care and treatment of laboratory animals. Male Sprague-Dawley ("S-D") rats were purchased from Charles River Laboratory (Wilmington, Mass.) and kept in the animal housing facilities with controlled relative humidity from about 20% to about 30%, at ambient temperature, and under approximately a 12-12 hour light-dark cycle, with free access to food and water. They were handled for about 5 to about 7 days before the procedure, to familiarize them with the experimental environment, so as to minimize stress-induced analgesia and to establish baseline behavioral parameters for each individual animal. At the time of surgery, animals weighed from about 280 grams to about 310 grams.

Three groups of eight rats each were studied under three respective conditions. Each group was the sum of two cohorts of four rats each, with each cohort being received from the supplier on the same day and being familiarized by handling and having surgery at the same time. Data from all eight rats in a group were analyzed together, without regard for cohort identification.

All rats received a thoracotomy as described below; a first group was injected with about 60 milligrams of microspheres of Example 1 at the incision site before the surgery, a second group with about 40 milligrams of placebo microspheres of Example 2 at the same location and time, and a third group with about 60 milligrams of microspheres of Example 1 at a distant, caudal location about 10 centimeters caudal from the incision site, where the anesthetized skin did not extend to the surgical field, but from which systemic uptake would be very similar. Injection of the third group was used to control for possible effects of systemic bupivacaine, released from microspheres of Example 1 and resorbed into the circulation.

Subcutaneous injections of the microspheres of Examples 1 and 2 were made through a 21 gauge, thin-walled, beveled needle (Becton-Dickinson) while the rats were under brief general anesthesia from muzzle-inspired sevoflurane. A volume of about 0.6 milliliters containing about 60 milligrams of bupivacaine base was also injected about 2 hours before the surgery, under the location of the intended incision and retraction in order to anesthetize a roughly circular area with a diameter of approximately 2 centimeters, the length of the incision for the thoracotomy.

Rats were briefly anesthetized with about 4% to about 5% sevoflurane (SEVORANE®, Abbott Laboratory, North Chicago, Ill., USA) before receiving intraperitoneal pentobarbital sodium (NEMBUTAL®, Akorn, Inc., Lake Forest, Ill.) at a dosage of about 60 milligrams per kilogram. Animals were then tracheally intubated. The anesthetized rats were placed in the supine position with a small pillow under the neck. An otoscope (Welch Allyn, Inc., Skaneateles Falls, N.Y.) with a number 3 speculum was introduced into the animal's oropharynx, and the tongue was gently retracted and fixed above the speculum by left index finger compression. A guide wire (spring-wire guide: 0.46 millimeters diameter, 25 centimeters length; Arrow International, Inc., Reading, Pa.) was introduced through the epiglottis, then vocal cords, into the trachea. The otoscope was removed over the wire, and a 16-gauge polyethylene catheter (ANGIOCATH® 1.7×51 millimeters INSYTE™ AUTOGUARD™ winged; BD Infusion Therapy Systems Inc., Sandy, Utah) was glided over the wire to its full length. The wire was removed, the catheter was connected to a Y-connector attached to tubing from a small animal pressure controlled ventilator (TOPO® 220; Kent Scientific Corporation, Torrington, Conn.), which was set at a respiratory rate of about 65 to about 80 breaths per minute. An isoflurane vaporizer (SURGIVET®) was connected to the intake of the ventilator to deliver a concentration of about 1.0% to about 1.5% of isoflurane in oxygen as necessary. A carbon dioxide analyzer (CAPSTAR-100®; IITC Inc., Woodland Hills, Calif.) was connected to the expiratory end to monitor end tidal carbon dioxide, which was maintained at about 25 millimeters mercury ("mm Hg") to about 40 mm Hg for the duration of the surgical procedure.

The anesthetized rats were placed in the left decubitus position with a pillow under the contralateral armpit to elevate the surgical field. The skin below the ear line and above the superior iliac crest was shaved on both sides. An approximately 3 centimeter incision was made in the skin of the right lateral chest wall along the fourth intercostal line, beginning from about 1 centimeter lateral to the midline and 1 centimeter below the inferior angle of the right scapula. The superficial and deep lateral thoracic muscles covering the ribs were incised and retracted to expose the intercostal muscles. An approximately 1 centimeter incision was made through the intercostal muscle and pleura along the cranial border of the fifth rib. The blunt tines of a small retractor (model 17003-03, Goldstein 3×3 sharp teeth with depth about 4.5 millimeters, teeth width about 6.5 millimeters; FST, Inc., Foster City, Calif.) were placed under the fourth and fifth ribs. The retractor was opened to separate the ribs by about 1 centimeter, and was left in place for about 60 minutes. During this time, the open wound was covered with wet-dressing gauze kept moist with sterile PBS. After about one hour, the retractor was closed and removed and the fourth and fifth ribs were approximated and ligated tightly with 4-0 VICRYL® sutures (Ethicon, Sommerville N.J.). Air was aspirated from the pleural cavity with a 5 milliliter syringe attached to the polyethylene tubing to restore normal intrapleural pressure. The superficial muscle covering the ribs was then apposed with 4-0 VICRYL® and the skin was closed with 3-0 PROLENE® sutures (Ethicon, Sommerville N.J.). The animals were allowed to recover, and the endotracheal catheter was removed once spontaneous breathing was re-established.

Pain thresholds were assayed daily or every other day during the entire testing period of about 31 days, including about 3 pre-operative days and about 28 post-operative days. Tests were performed at the same time of day for about 3 hours for each separate cohort. The threshold force necessary to elicit any response from a rat was determined by pressing against the shaved thoraco-lumbar dorsal area of the rat with a series of single von Frey hair monofilaments ("VFH"). Each rat was tested alone by probing with a VFH while loosely constrained in a "holding chamber" that allowed the rats to re-orient their bodies, and thus escape the potentially painful stimulus, without running away. Individual VFH filaments were applied starting from the lightest force of about 1 gram mass ("gm") to about 2 gm, and progressing in a series of increasing thickness/force until a response was elicited, but limited to about 15 gm. Rats that did not respond even to this highest force were assigned a threshold of 15 gm, since stronger forces caused local swelling/inflammation of the skin after repeated stimulation.

Once any response was elicited, the next stimulation was by the preceding ineffective force VFH, then again by the effective force. Threshold was defined as the weakest force that could reliably elicit a response, e.g. 3 responses from 3 pokes.

As noted above, rats were acclimated for about 5 days to about 7 days before the surgery, to abolish "stress-induced analgesia" and allow for the establishment of a stable pre-operative baseline threshold. This threshold was calculated from the average of thresholds measured on each of the 3 days preceding the operation.

Since the nature of the response at threshold changes after surgery, responses were characterized by the Qualitative Hyperalgesic Profile ("QHP"). Behavior was classified according to the following scoring system of grades as illustrated in Table 1 below:

TABLE 1

| Grade | Behavioral response to Tactile Stimulation |
|---|---|
| 0 | No response |
| I | Brief contractions of the local subcutaneous muscles. |
| II | Grade I and brisk lateral "escape" movement and/or a 180° rotation of the trunk. |
| III | Grade II and whole body shuddering, and scratching and squealing. |

These patterns of behavior were characteristic of different stages of pre- and post-operative "pain." Grades 0 and I were the only responses that occurred in the intact, pre-operative skin, and were elicited by VFH forces of about 15 gm. After surgery, Grades II and III were observed, in response to threshold stimulation, e.g., about 3 gm.

Figure 5:
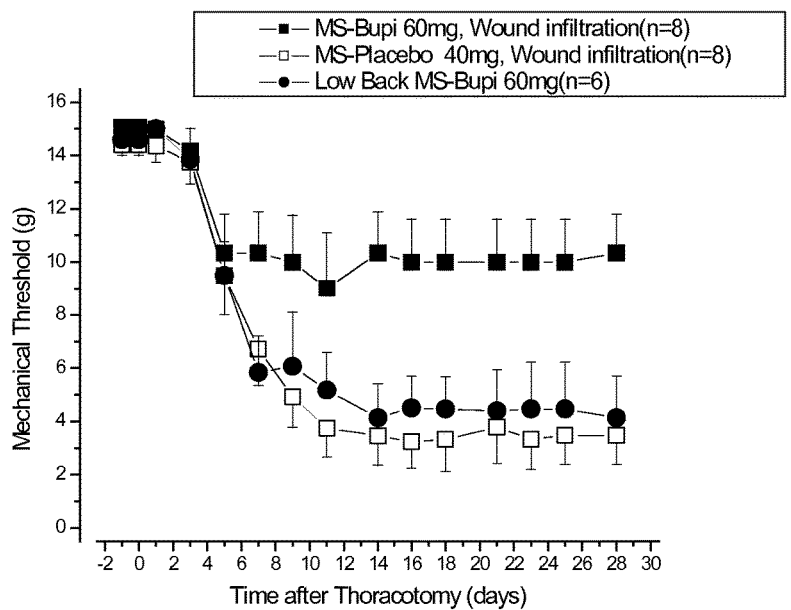
FIG. 5 is a plot of mechanical nocifensive threshold responses of three groups of laboratory rats treated in accordance with the present disclosure.

Plots of mechanical threshold responses of the three groups of rats injected pre-operatively with microspheres of Example 1 and placebo microspheres of Example 2 were recorded and plotted for 28 days as shown in FIG. 5. With reference to FIG. 5, the solid square data points represent the threshold response of the first group of rats, which were injected with microspheres of Example 1 at the incision site. The blank square data points represent the threshold response of the second group of rats, which were injected with placebo microspheres of Example 2 at the incision site. The solid circular data points represent the threshold response of the third group of rats, which were injected with microspheres of Example 1, but about 10 centimeters caudal from the incision site.

It was observed that in the rats of all three groups, the threshold for the first three post-operative days was at about 15 gm. However, the threshold for the second and third groups then dropped to about 3 gm and about 5 gm, respectively, for the remaining approximately 25 days. In contrast, in the first group the initial drop in threshold was arrested after about 4 days, at about 10 gm, and remained there for the next 24 days of testing. The possibility that this anti-hyperalgesic effect could result from systemically distributed bupivacaine, released from the microspheres and resorbed by the local, cutaneous and subcutaneous circulation, was tested by the third group, which was injected at the same pre-operative time but at a more caudal location. The effects of this treatment were not significantly different from those of the group having the placebo microspheres of Example 2 at the wound site, and ruled out a contribution of systemic bupivacaine to post-operative anti-hyperalgesia.

FIGS. 6A-H show a plurality of plots of average threshold responses of individual rats numbered 1 through 8 of the first group treated with Example 1 microspheres. Each of the eight rats of the first group that received microspheres of Example 1 showed one of three patterns of time-course of threshold change. Course 1: threshold fell to about 8 gm by about the fifth or sixth day post-operatively and remained there, for example, rats nos. 1-3. Course 2: threshold remained at the pre-operative baseline of 15 gm, with no sensitivity, as observed in rats nos. 5-7. Course 3: threshold fell to a low value of about 2 gm, and remained there as observed in rat no. 8. Rat no. 8 had an unusually low baseline threshold of about 10 gm and showed the persistent fall to about 2 gm after surgery. Rat no. 4 showed a transient fall of threshold to about 2 gm at about day 10, but then reversed to and remained at about 8 gm by about day 16.

FIGS. 7A-H shows a plurality of plots of individual rats numbered 1 through 8 of the second group also treated with Example 2 microspheres. Each of the eight rats of the second group that received placebo microspheres of Example 2 showed one of four patterns of time-courses of threshold change. Course 1: rats nos. 1 and 6 showed a decrease to intermediate thresholds of about 8 gm. Course 2: all of the rats showed a drop in threshold after surgery. Course 3: rats nos. 2, 4, 5, and 7 showed a fall to the same low level of about 1 gm. Course 4: rats nos. 3 and 8 had thresholds that fell to only 4 gm and remained there through approximately day 28.

The distribution of threshold courses among first and second groups is shown in Table 2 below.

TABLE 2

| | Number of rats in each course | |
|---|---|---|
| Time Course | First Group | Second Group |
| 1 | 3 | 2 |
| 2 | 3 | 0 |
| 3 | 1 | 4 |
| 4 | 0 | 2 |

It was also observed that pre-operative injection of microspheres of Example 1 lessened pain as indicated by the QHP. With reference to Table 1 above, the baseline period of all the rats in any of the three groups showed either Grade I or Grade 0 responses; that is, either the rats had no response or only a contraction of the local back muscles. After thoracotomy, however, Grades II and III were observed to appear at threshold and became the predominant behavioral expression.

Figure 6A:
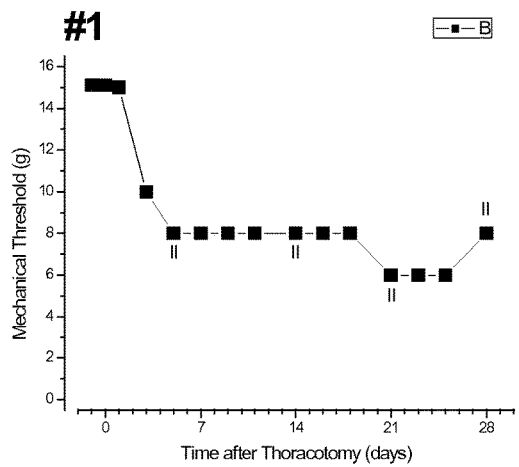
FIGS. 6A-H are a plurality of plots of threshold responses of individual tested rats after injection of bupivacaine microspheres in accordance with the present disclosure.
Figure 6B:
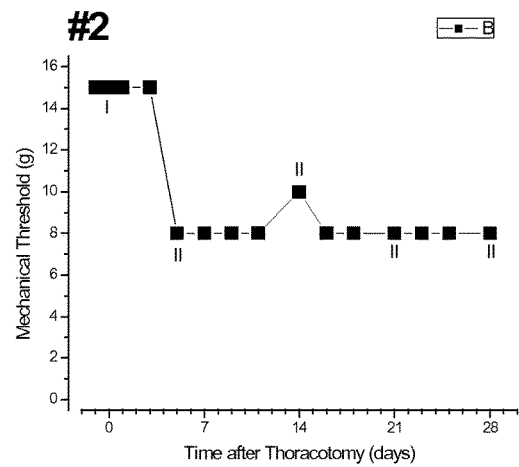
Figure 6C:
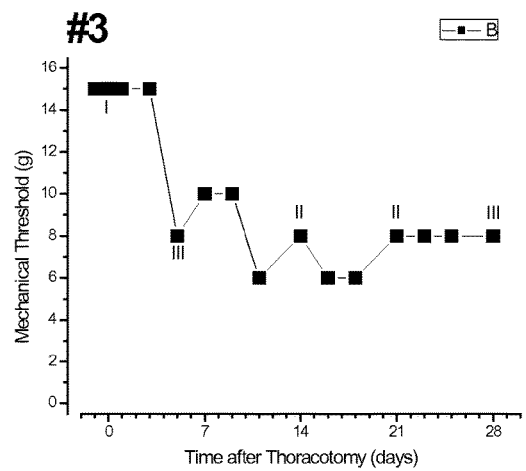
Figure 6D:
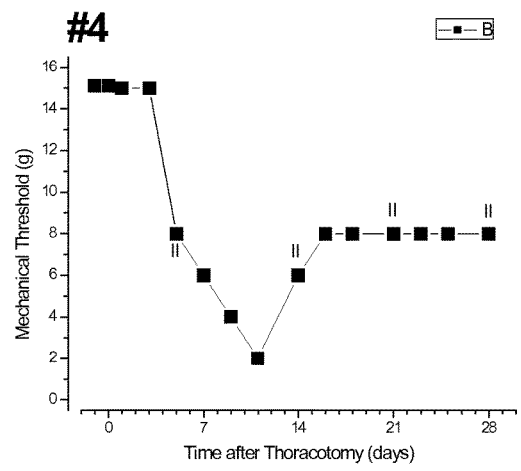
Figure 6E:
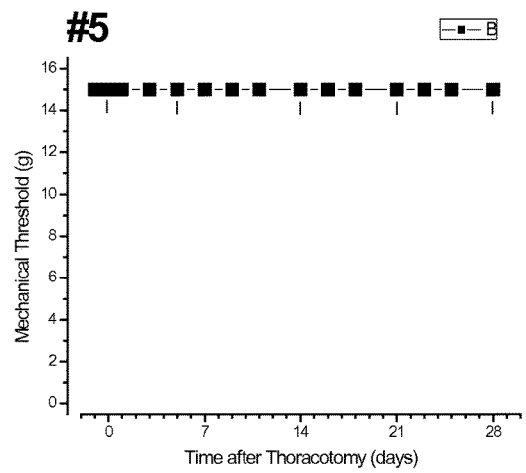
Figure 6F:
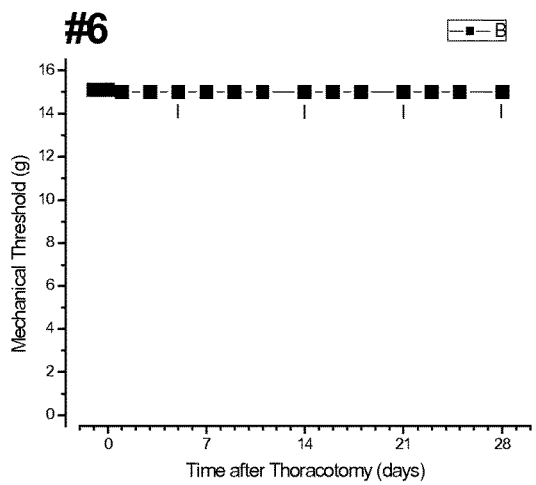
Figure 6G:
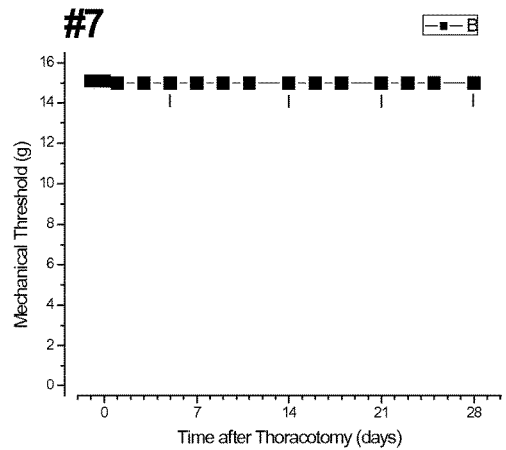
Figure 6H:
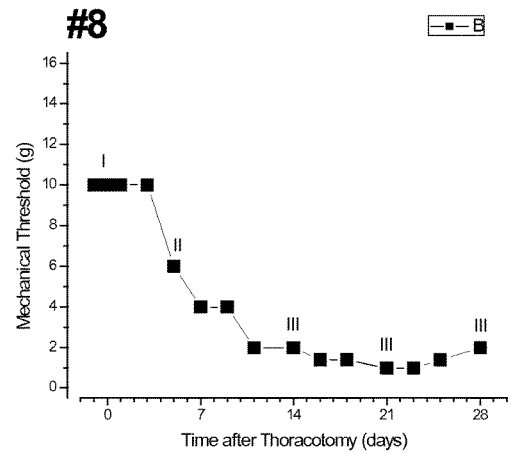
Figure 7A:
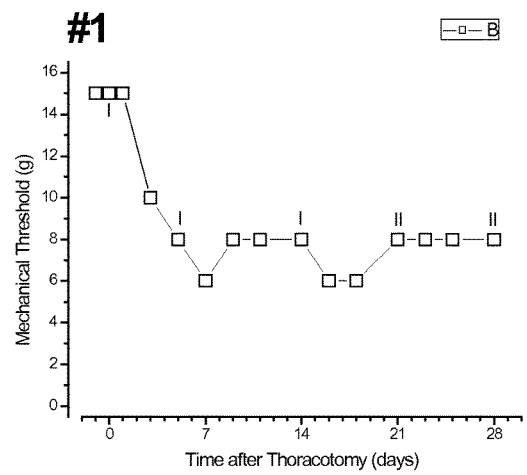
FIGS. 7A-H are a plurality of plots of threshold responses of individual tested rats after injection of placebo microspheres in accordance with the present disclosure.
Figure 7B:
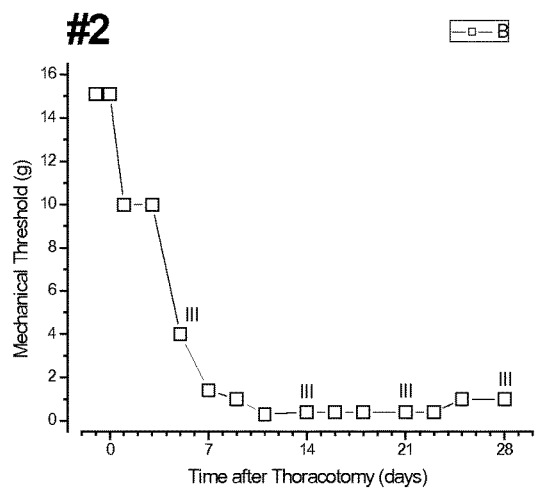
Figure 7C:
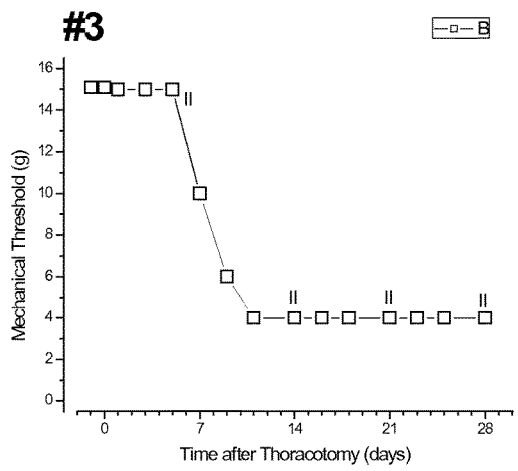
Figure 7D:
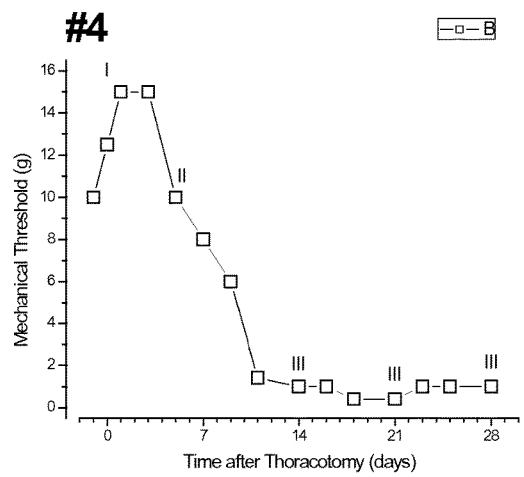
Figure 7E:
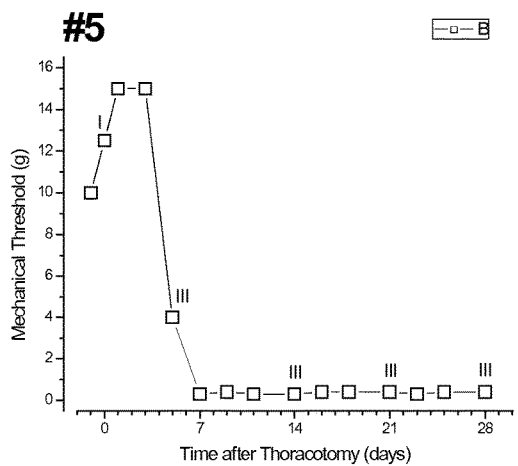
Figure 7F:
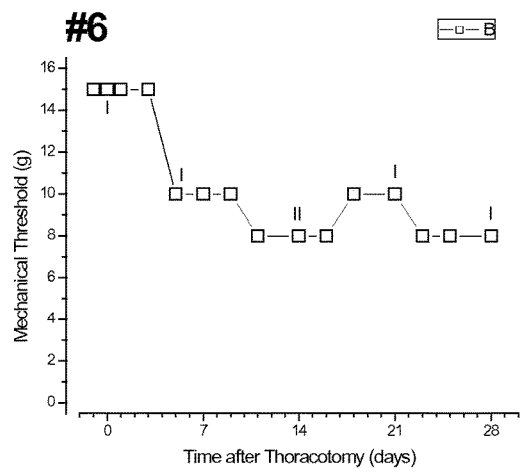
Figure 7G:
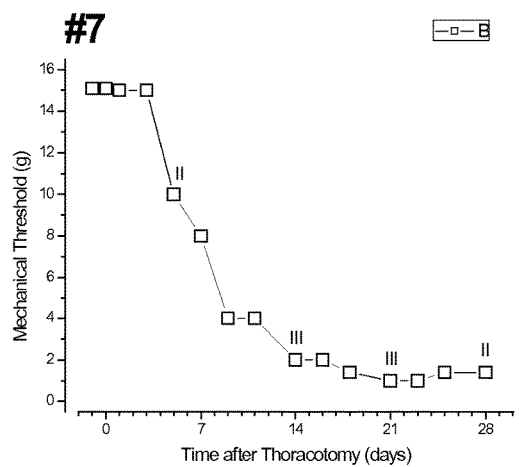
Figure 7H:
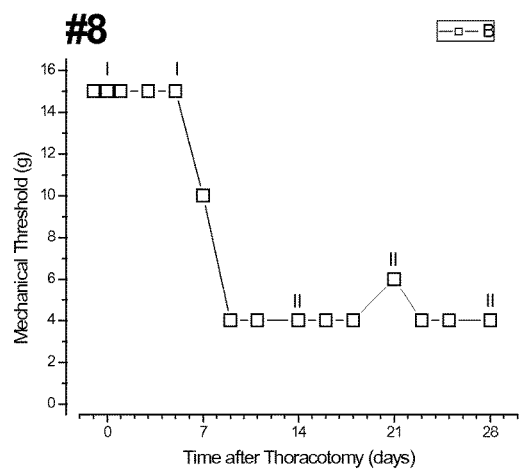
Figure 8A:
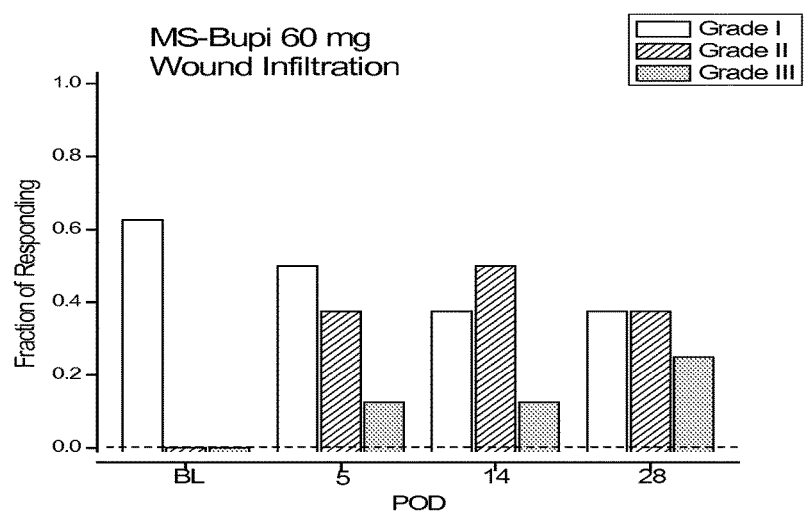
FIGS. 8A-C are a plurality of bar graphs of qualitative hyperalgesic profiles of three groups of laboratory rats tested in accordance with the present disclosure.
Figure 8B:
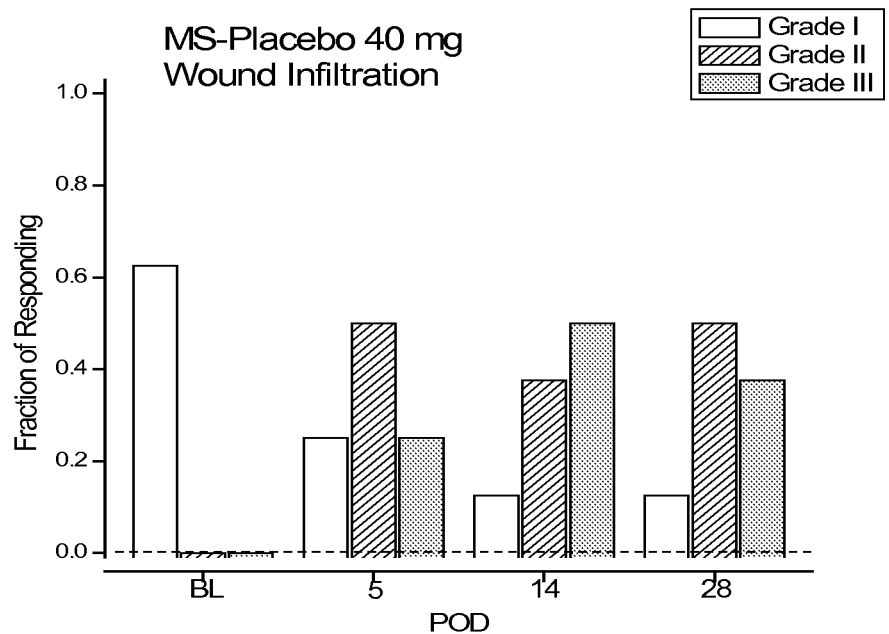
Figure 8C:
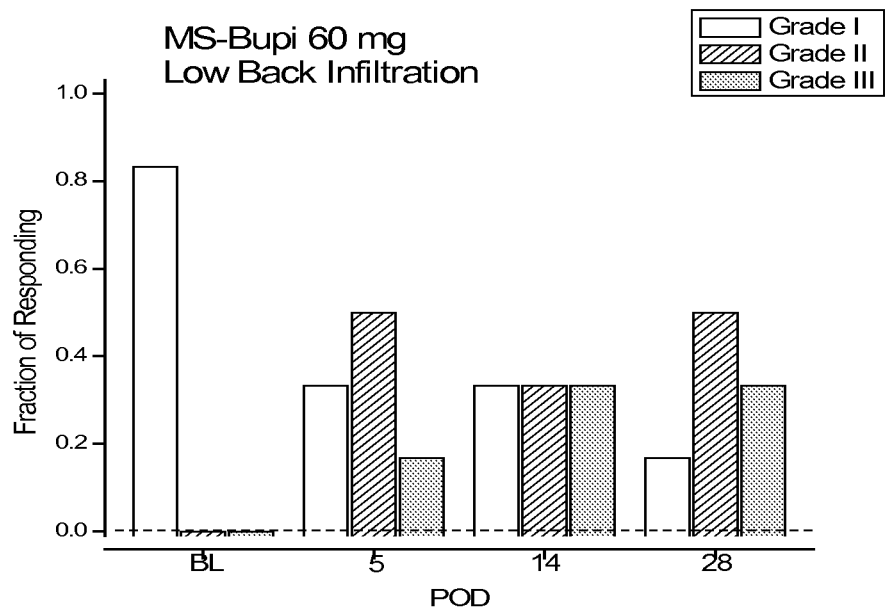

The QHP grades of the individual rats at different post-operative stages are shown in the plots of FIGS. 8A-C. FIG. 8A shows a bar graph of QHP responses taken prior to surgery and days 5, 14, and 28 post-operatively, respectively, for the first group. In the first group, it was observed that three of the eight rats showed Grade I behavior while the remaining five showed Grade II and III behaviors. However, the three rats, nos. 5-7, which retained their QHP Grade of I were the same rats which showed no drop in threshold after surgery, as shown in FIGS. 6E-G. Thus, based on the VFH forces required to elicit the higher QHP responses, the microspheres of Example 1 were successful in treating chronic post-surgical pain for approximately 28 days.

FIG. 8B shows a bar graph of QHP responses taken prior to surgery and days 5, 14, and 28, respectively, for the second group. In this group, 14 and 28 days after surgery, Grades II and III were observed in seven of the eight rats in the second group, with only a single rat showing Grade I behavior. FIG. 8C shows a bar graph of QHP responses taken prior to surgery and days 5, 14, and 28, respectively, for the third group. The QHP distribution at day 28 in this group was almost identical to that of the second group.

The microspheres of Example 1 were also tested for sciatic nerve block and for subcutaneous infiltration anesthesia in rats. Sciatic nerves were injected with nominal doses of microspheres of Example 1, having about 40 milligrams of bupivacaine, by injection as a single bolus of about 0.4 milliliters. Analysis of the material retained in the injecting syringe showed that the injected dose was about 34±1 milligrams of bupivacaine. Nociceptive block to paw pinch showed complete unresponsiveness for about 23±7 hours; motor block indicated by total flaccid paralysis lasted for about 12±10 hours. Half-recovery of these respective functions occurred at about 42±6 hours and 36±3 hours, and normal, pre-block function was restored by about 63±8 hours for nociception and about 56±7 hours for motor block. By comparison, injection of about 0.4 milliliters of about 0.5% by weight aqueous bupivacaine solution gave complete blocks for only about 0.5 hours to about 1 hours for nociception and about 1 hour for motor functions, with complete recovery by about 3 hours for both functions. Microspheres of Example 2 caused no functional deficits.

Microspheres of Example 1 were also tested for anti-hyperalgesic effects after rodent surgery. Paw incision in a lateral region innervated exclusively by the sciatic nerve resulted in about 3 day to about 4 days of tactile allodynia and hyperalgesia in rats of the third group, as tested by VFH applied to the plantar paw next to the incision. If microspheres of Example 1 were injected at the sciatic nerve approximately 1.5 hours before the surgery, the subsequent post-operative hyperalgesia was suppressed for about 4 days. In contrast, nerve block by 0.5% by weight aqueous bupivacaine solution suppressed post-operative hyperalgesia for about 6 hours. Microspheres of Example 2 were ineffective against post-incisional pain.

In a second surgical scenario, Microspheres of Example 1 were injected as a subcutaneous infiltration in the thoraco-lumbar region before an incision and blunt dissection of the back skin. Microspheres of Example 1, including about 40 milligrams of bupivacaine, were injected as a single bolus of about 0.4 milliliters. The injection produced anesthesia to VFH pokes at the injected area for about 6 hours and anesthesia to pin pricks for about 12 hours. Post-operative allodynia and hyperalgesia in this model lasted for about 14 days, but were suppressed for approximately 5 days and 3 days, respectively, by microspheres of Example 1 injected approximately 2 hours before surgery. About 0.4 milliliters of 0.5% by weight aqueous bupivacaine solution was ineffective in reducing post-operative hypersensitivity, just as the microspheres of Example 2 were also ineffective. In addition, injections of the same dose of microspheres of Example 1 on the back side contralateral to the incision site had no effect on post-operative pain, suggesting that systemically distributed local anesthetic could not alone yield any therapeutic effect.

Comparative Example 1

This Example describes release kinetics of bupivacaine from EXPAREL® particles, a bupivacaine liposome injectable suspension of particles (Pacira Pharmaceuticals, Inc., San Diego, Calif.). EXPAREL® includes bupivacaine encapsulated in DEPOFOAM® particles (Pacira Pharmaceuticals, Inc., San Diego, Calif.), which is a multi-vesicular suspension of particles composed of lipids, such as phospholipids (e.g., dioleoylphosphatidylcholine (DOPC), dierucoylphosphatidylcholine (DEPC), dipalmitoylphosphatidylglycerol (DPPG)), cholesterol and triglycerides (e.g., triolein, tricaprylin).

The EXPAREL® suspension included about 97% by weight aqueous solution of bupivacaine and about 3% lipids and was expected to be fully biodegradable. The EXPAREL® suspension was suspended in 0.9% by weight saline solution for injection.

The mean diameter of EXPAREL® particles was about 31.2±17.8 micrometers, as measured by phase contrast microscopy. Analysis of bupivacaine content of EXPAREL® particles was about 261±18 milligrams per 20 milliliters suspension, equivalent to about 1.33% by weight of the suspension. The bupivacaine loading of DEPOFOAM® particles was thus about 47.4±3.3% by weight of the suspension, and the commercially available EXPAREL® particles contained about 13±0.9 milligram per milliliter of bupivacaine.

Release kinetics of bupivacaine from commercially available EXPAREL® particles was measured by dialysis in PBS at about 37° C. and demonstrated a relatively rapid initial release of about 10% of bupivacaine for approximately the first 50 hours, followed by a slower phase during which about another 25% of the bupivacaine was released over 300 hours; another 50% of the contained bupivacaine was released rapidly over about the next 100 hours, and the remaining drug then slowly released over about the next 300 hours. In total, about 800 hours was required for all of the bupivacaine to be released. The highly unconventional kinetics of release implies either a lack of uniformity in the distribution of bupivacaine within the DEPOFOAM® particles, or a lack of homogeneity in the different sizes and compositions of DEPOFOAM® bupivacaine. Such a lack of homogeneity in particle size is also suggested by the large variance in the mean diameter as noted above.

The anti-nociceptive activity of EXPAREL® particles was also tested. The latency for leg withdrawal in male S-D rats from a noxious heat stimulus of about 56° C. applied to the plantar surface of the paw was used to test the duration of functional sciatic nerve block achieved using EXPAREL®. The normal latency for paw withdrawal was about 2 seconds and "maximal sensory blockade" was characterized by a latency of about 12 seconds. Sensory blockade of about 0.6 milliliters of EXPAREL® containing about 7.8 milligrams of bupivacaine, injected next to the sciatic nerve of an adult male S-D rat weighing from about 310 grams to about 420 grams, which was equivalent to about 25 milligrams of bupivacaine per kilogram, was determined by the time from injection until the latency returned to about 7 seconds, half way back to the pre-injection latency of about 2 seconds. By this criterion, the sensing block from EXPAREL® lasted about 240 minutes, and that from 0.6 milliliter solution of about 0.5% by weight bupivacaine, which was used as a control, lasted about 120 minutes.

Comparative Example 2

This Example describes release kinetics of bupivacaine from bupivacaine polyester microspheres from Purdue Pharma L.P., Stamford, Conn.

Purdue microspheres were made of PLGA polymers, encapsulating bupivacaine. The microspheres were tested in vivo and contained PLGA including PLA:GA at a ratio of about 65:35, encapsulated bupivacaine at about 75±2% by weight of the microspheres, and dexmethasone at about 0.05% by weight of the microspheres. Dexmethasone was used to increase duration of local anesthesia by the microspheres in vivo to more than about 1 day. However, inclusion of dexmethasone did not affect the bupivacaine release kinetics in vitro.

The Purdue microspheres had a mean diameter of about 76 micrometers. Release kinetics of the microspheres appeared to be dependent on the PLA:GA ratio. Pure PLA microspheres released about 100% of bupivacaine in less than about 1 day. In contrast, microspheres containing PLGA at a ratio of PLA:GA of about 50:50 released about 100% of bupivacaine with approximately first order exponential kinetics having a half-life of about 2 days. It was also observed that there was an initial "burst release" wherein 25% of bupivacaine was released in the first several hours. This same burst occurred for the microspheres having PLGA at a ratio of about 75:25, followed by fairly uniform release kinetics approximately over the next 10 days, but ultimately only about 80% of the included drug was delivered by this formulation. The microspheres having PLGA at a ratio of about 65:35 showed no burst release, but also only released approximately 80% of the loaded bupivacaine.

The Purdue microspheres have been tested for local anesthesia using thermal latency. Sciatic nerve blocks were accomplished with about 150 milligrams per kilogram dosage of bupivacaine injected next to the sciatic nerve of male S-D rats. Block durations were from about 3 hours to about 6 hours for preparations that did not contain dexmethasone, but were extended to about 70 hours to about 100 hours when dexmethasone was included at a concentration of about 0.05% by weight of the Purdue microspheres. Motor block, determined by the rat's ability to bear weight on its blocked leg, was somewhat longer lasting and was also greatly extended by inclusion of dexmethasone up to about 160 hours.

Local inflammation caused by the Purdue microspheres was observed and was believed to be related to the brief block duration. This was confirmed by injecting the Purdue microspheres around the intercostal thoracic nerves of sheep. Duration of block for a noxious pinch to the skin overlying the rib cage was extended by the inclusion of dexamethasone at a concentration of about 0.05% by weight of the Purdue microspheres. Doses of about 40 milligrams per kilogram or about 8 milligrams per nerve, since 5 nerves were injected for each block, lasted about 2±1days and increased by inclusion of dexamethasone to about 10±3 days. Histology of muscle taken from the tissues where Purdue microspheres without dexmethasone were injected showed intense invasion of neutrophils (PMNs), as early as about 7 hours after injection and evolved into a granulomatous infiltration with many macrophages present by about 4 days. In contrast, the histopathology of tissues where Purdue microspheres with dexmethasone were injected was almost normal. The correlation between increased block duration and decreased local inflammation provided support for a causative relationship. This relationship suggested that the environment around the inflamed region, e.g., the slightly acidic pH, from about 6.9 to about 7.2, compared to pH of about 7.4 in un-inflamed tissue, decreased the ratio of neutral, nerve-permeant, bupivacaine species to charged, nerve-impermeant species (having basic pH of about 8.1), and thus decreased the neural content and the duration of blockade.

Discussion

This Discussion compared physical, chemical, and drug-release properties of the microspheres of Example 1, the composition of Comparative Example 1, and the microspheres of Comparative Example 2, as well as their ability to effect numbness in vivo in pre-clinical, animal studies, and their capacity to reduce experimental post-operative pain.

Controlled-release microspheres of Comparative Example 2 achieved the release profile solely due to the incorporation of dexamethasone in the formulation as the second active pharmaceutical ingredient. Microspheres of Example 1 demonstrated a significant reduction of pain in rats lasting several days, after 24 hours, with the use of bupivacaine as the only active pharmaceutical ingredient in the microsphere formulation.

The drug-loading levels achieved with microspheres of Comparative Example 2 and that of the microspheres of Example 1 were both relatively high, about 75% and about 60%, respectively. In addition, the total drug dosage administered per animal was similar as well, about 150 milligrams per kilogram with microspheres of Comparative Example 2 and about 133.3 milligrams drug per kilogram with the microspheres of Example 1. Yet, microspheres of Comparative Example 2 had no reported effect on chronic pain, whereas the microspheres of Example 1 mitigated post-operative chronic pain for about 28 days. Thus, the difference in performance is believed to be due on the differences in kinetics of release, impacting the bioavailability of bupivacaine and the duration of in vivo efficacy.

A comparison of the release kinetics of the microspheres of Comparative Example 2 suggested that about 75% of the release of bupivacaine in vitro occurred over about 7 days. In contrast, in microspheres of Example 1, 75% of bupivacaine was released in vitro in about 3 days. Therefore, the effective rate of release differs by a factor of more than about 2. However, this average difference contrasts with approximately the first 6 to 12 hours of bupivacaine release. With microspheres of Comparative Example 2, a "burst effect" was observed in vitro, whereas the microspheres of Example 1 had no pronounced burst effect but rather a relatively constant release rate of approximately 0.6 to 0.75 milligrams per hour as discussed above with respect to FIG. 4. Consistent with this observation, it is believed that reducing the burst effect might prolong in vivo efficacy for bupivacaine, although there seems to be no suggestion that reducing burst effect could impact chronic pain.

For the microspheres of Example 1, the uniform distribution of both polymer and bupivacaine throughout the microsphere cross-section, based on the Raman spectroscopy data of FIG. 2B and the low porosity for these microspheres (gas physisorption data), is believed to have contributed to achieving a relatively consistent release rate for bupivacaine. The Raman spectroscopy and porosity data were also consistent with a surface erosion and diffusion-based mechanism for bupivacaine release, an inference supported by the relatively good fit for the formulation with the Higuchi model, with $R^2$ being about 0.985, for diffusion-based controlled release systems.

The composition of Comparative Example 1 was also injected into rabbits and dogs and blood levels of bupivacaine were measured over the following several days. Subcutaneous doses were injected at the left and right sides around the dorsal midline containing bupivacaine at concentrations of about 9, 18, and 30 milligrams per kilogram, delivered as different volumes or dilutions of about 25 milligrams per milliliter. Plasma bupivacaine in the rabbits reached a peak value of about 213±145, 147±60, and 94±45 nanograms per milliliter from single bolus injections of 9, 18 and 30 milligrams per kilogram, respectively. This reverse relationship between dose given and plasma level achieved may have resulted from the use of different volumes and dilutions to deliver the different doses, affecting surface-to-volume ratio for subcutaneous spread of the different doses and the local concentrations with differing effects on local vascular tone and resulting drug removal. Peak plasma values occurred at about 1 hour to about 4 hours after injection of doses at about 9 milligrams per kilogram and about 18 milligrams per kilogram, respectively, and at about 26±24 hours after a dose of about 30 milligrams per kilogram.

The analogous subcutaneous injections in dogs, with higher total doses due to their greater weights, resulted in peak plasma concentrations of bupivacaine of about 488±335, 560±299, and 633±280 nanograms per milliliter, respectively, single injections of about 9,18 and 30 milligrams per kilogram. The doses of about 9 milligrams per kilogram and 18 milligrams per kilogram led to peak values in plasma occurring at about 0.5 hours and the dose of about 30 milligrams per kilogram led to a peak at about 48±30 hours.

Thus, neither the composition of Comparative Example 1 nor the microspheres of Comparative Example 2 had any impact on treating chronic pain. Although the composition of Comparative Example 1 and the microspheres of Comparative Example 2 provide sustained release of bupivacaine,e they had no effect on relieving pain after completely releasing bupivacaine, which occurred after the first few days. Only the microspheres of Example 1 as described above, were shown to have an impact on chronic pain approximately throughout 28 days. The data collected in Example 3, illustrates that the microspheres of Example 1 possess unexpected properties for treating chronic pain that are absent from the composition of Comparative Example 1, the microspheres of Comparative Example 2 and other sustained release bupivacaine formulations.

It will be appreciated that of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, or material.

What is claimed is:

1. A method for treating chronic pain comprising:
   implanting at least one microsphere at a treatment site, the microsphere comprising:
      at least one local anesthetic and poly(lactic-co-glycolic acid) including polylactic acid and glycolic acid at a ratio of about 75:25;
   wherein about 75% of the at least one local anesthetic is released by about 72 hours and from about 80% to about 90% of the at least one local anesthetic is released by about 120 hours; and
   relieving chronic pain for at least 28 days.

2. The method according to claim 1, wherein the at least one microsphere is implanted preoperatively.

3. The method according to claim 1, wherein the at least one microsphere is implanted postoperatively.

4. The method according to claim 1, further comprising forming a suspension including the at least one microsphere.

5. The method according to claim 4, further comprising injecting the suspension into the treatment site.

6. The method according to claim 4, further comprising depositing the suspension on at least a portion of a medical device to form a film thereon, the film including the at least one microsphere particle.

7. The method according to claim 1, wherein the at least one local anesthetic is bupivacaine.

8. The method according to claim 1, wherein the at least one local anesthetic is present in amount of about 60% by weight of the at least one microsphere.

9. The method according to claim 1, wherein implanting at least one microsphere at a treatment site includes implanting at least one microsphere wherein the at least one local anesthetic and the poly(lactic-co-glycolic acid) are uniformly distributed throughout the at least one microsphere.

10. The method according to claim 1, wherein implanting at least one microsphere at a treatment site includes implanting at least one microsphere wherein the at least one microsphere is porous with pores being from about 0.1% to about 15% by volume of the at least one microsphere.

11. The method according to claim 1, wherein the treatment site is a surgical site of at least one of herniorraphy, thoracotomy, or joint arthroscopy.

12. A method for treating chronic pain comprising:
   implanting at least one microsphere at a surgical site of at least one of herniorraphy, thoracotomy, or joint arthroscopy, the microsphere comprising:
      at least one local anesthetic and poly(lactic-co-glycolic acid) including polylactic acid and glycolic acid at a ratio of about 75:25;
   wherein about 75% of the at least one local anesthetic is released by about 72 hours and from about 80% to about 90% of the at least one local anesthetic is released by about 120 hours; and
   reducing chronic pain associated with at least one of herniorraphy, thoracotomy, or joint arthroscopy for at least 28 days.

13. The method according to claim 12, wherein the at least one microsphere is implanted preoperatively.

14. The method according to claim 12, wherein implanting at least one microsphere at a treatment site includes implanting at least one microsphere wherein the at least one local anesthetic and the poly(lactic-co-glycolic acid) are uniformly distributed throughout the at least one microsphere.

15. The method according to claim 12, wherein implanting at least one microsphere at a treatment site includes implanting at least one microsphere wherein the at least one microsphere is porous with pores being from about 0.1% to about 15% by volume of the at least one microsphere.

* * * * *